(12) United States Patent
Nichols et al.

(10) Patent No.: US 11,970,521 B2
(45) Date of Patent: Apr. 30, 2024

(54) NEUROPROTECTIVE BETA AMYLOID CORE PEPTIDES AND PEPTIDOMIMETIC DERIVATIVES

(71) Applicants: ARIZONA BOARD OF REGENTS ON BEHALF OF THE UNIVERSITY OF ARIZONA, Tucson, AZ (US); UNIVERSITY OF HAWAII, Honolulu, HI (US)

(72) Inventors: Robert A. Nichols, Honolulu, HI (US); Kelly Forest, Honolulu, HI (US); Victor J. Hruby, Tucson, AZ (US)

(73) Assignees: ARIZONA BOARD OF REGENTS ON BEHALF OF THE UNIVERSITY OF ARIZONA, Tucson, AZ (US); UNIVERSITY OF HAWAII, Honolulu, HI (US)

( * ) Notice: Subject to any disclaimer, the term of this patent is extended or adjusted under 35 U.S.C. 154(b) by 328 days.

(21) Appl. No.: 16/326,777

(22) PCT Filed: Aug. 15, 2017

(86) PCT No.: PCT/US2017/046953
§ 371 (c)(1),
(2) Date: Feb. 20, 2019

(87) PCT Pub. No.: WO2018/038973
PCT Pub. Date: Mar. 1, 2018

(65) Prior Publication Data
US 2019/0233487 A1 Aug. 1, 2019

Related U.S. Application Data

(60) Provisional application No. 62/377,556, filed on Aug. 20, 2016.

(51) Int. Cl.
| | | |
|---|---|---|
| *C07K 14/47* | (2006.01) | |
| *A61K 9/00* | (2006.01) | |
| *A61K 38/00* | (2006.01) | |
| *A61K 38/17* | (2006.01) | |
| *A61P 25/28* | (2006.01) | |
| *C07K 14/00* | (2006.01) | |

(52) U.S. Cl.
CPC ........ *C07K 14/4711* (2013.01); *A61K 9/0019* (2013.01); *A61K 9/0053* (2013.01); *A61K 38/00* (2013.01); *A61K 38/1716* (2013.01); *A61P 25/28* (2018.01); *C07K 14/00* (2013.01)

(58) Field of Classification Search
CPC ...... C07K 14/00; C07K 14/4711; C07K 7/06; C07K 7/08; C07K 7/64; C07K 7/00; C07K 7/02; C07K 7/54; C07K 1/006; C07K 1/1072; A61K 38/00; A61K 38/04; A61K 38/1716; A61P 25/28
See application file for complete search history.

(56) References Cited

U.S. PATENT DOCUMENTS

| | | | | |
|---|---|---|---|---|
| 6,713,450 | B2 * | 3/2004 | Frangione | C07K 14/4711 424/185.1 |
| 2006/0234947 | A1 * | 10/2006 | Gazit | C07K 5/0823 514/17.8 |
| 2007/0264276 | A1 | 11/2007 | Chalifour et al. | |
| 2009/0123488 | A1 | 5/2009 | Goldstein | |
| 2010/0130416 | A1 * | 5/2010 | Paris | C07K 14/4711 435/7.1 |
| 2011/0076323 | A1 | 3/2011 | Monsonego et al. | |
| 2013/0136747 | A1 | 5/2013 | Bardroff et al. | |
| 2013/0259851 | A1 * | 10/2013 | Zangemeister-Wittke | A61K 38/51 424/94.5 |
| 2014/0287022 | A1 * | 9/2014 | Fujii | A61K 9/1277 424/450 |

FOREIGN PATENT DOCUMENTS

| | | | | |
|---|---|---|---|---|
| WO | WO-02096937 A2 * | 12/2002 | | C07K 14/4711 |
| WO | WO-2004013172 A2 * | 2/2004 | | C07K 14/4711 |
| WO | WO2004058239 A1 | 7/2004 | | |
| WO | WO-2006087550 A2 * | 8/2006 | | A61P 25/14 |

OTHER PUBLICATIONS

Bose PP et al. Poly-N-methylated amyloid-beta peptide (Abeta) C-terminal fragments reduce Abeta toxicity in vitro and in *Drosophila melanogaster*. J. Med. Chem. 2009, 52, 8002-8009. (Year: 2009).*
Chatterjee J et al. N-methylation of peptides: A new perspective in medicinal chemistry. Acc. Chem. Res. 2008, 41(10), 1331-1342. (Year: 2008).*
Istrate AN et al. Interplay of histidine residues of the Alzheimer's disease Abeta peptide governs its Zn-induced oligomerization. Scientific Rep. Feb. 2016, 6:21734, 14 pages. (Year: 2016).*
Kokkoni N et al. N-methylated peptide inhibitors of beta-amyloid aggregation and toxicity. Optimization of the inhibitor structure. Biochemistry, 2006, 45, 9906-9918. (Year: 2006).*
Cruz M et al. Inhibition of beta-amyloid toxicity by short peptides containing N-methyl amino acids. J. Peptide Res. 2004, 63, 324-328. (Year: 2004).*

(Continued)

*Primary Examiner* — Kimberly Ballard
(74) *Attorney, Agent, or Firm* — NGUYEN TARBET LLC

(57) ABSTRACT

Peptide analogues of β-amyloid and methods of using said analogues for neuroprotection are described herein. The β-amyloid peptide analogues have a sequence that is at least 50% identical to an N-terminal β-amyloid core fragment. A pharmaceutical composition of the β-amyloid peptide analogues in a pharmaceutically acceptable carrier can be administered to a subject for neuromodulation. The β-amyloid peptide analogues, while lacking neurotoxicity, effectively provides for protective activity against β-amyloid toxicity.

16 Claims, 13 Drawing Sheets

Specification includes a Sequence Listing.

(56) References Cited

OTHER PUBLICATIONS

Kapurniotu A et al. Structure-based design and study of non-amyloidogenic, double N-methylated IAPP amyloid core sequences as inhibitors of IAPP amyloid formation and cytotoxicity. J. Mol. Biol. 2002, 315, 339-350. (Year: 2002).*

Gordon DJ et al. Inhibition of beta-amyloid(4) fibrillogenesis and disassembly of beta-amyloid(40) fibrils by short beta-amyloid congeners containing N-methyl amino acids at alternative residues. Biochem. 2001, 40:8237-8245. (Year: 2001).*

Rajasekhar K et al. Rationally designed peptidomimetic modulators of Amyloid-beta toxicity in Alzheimer's disease. Sci. Reports, Jan. 2015, 5:8139, 9 pages. (Year: 2015).*

Lawrence et al., "Regulation of Presynaptic Ca2!, Synaptic Plasticity and Contextual Fear Conditioning by a N-terminal!-Amyloid Fragment" J. Neuroscience, 34(43), 2014.

Arora et al., "Impact of Sustained Exposure to B-Amyloid on Calcium Homeostasis and Neuronal Integrity in Model Nerve Cell System Expressing $\alpha 4\beta 2$ Nicotinic Acetylcholine Receptors" J. Biol. Chem, 288, 16, 2013.

Wong et al. "Genetically engineered mouse models of neurodegenerative diseases", Nature Neurosci. 2002, 5, 633-639.

Ingelsson et al. "Early A$\beta$ accumulation and progressive synaptic loss, gliosis, and tangle formation in AD brain", Neurol. 2004, 62, 925-932.

Tong et al., "Role of Key Aromatic Residues in the Ligand-binding Domain of $\alpha 7$ Nicotinic Receptors in the Agonist Action of $\beta$-Amyloid" J. Biol. Chem, 286, 39, 2011.

Arora et al., "Nicotinic Acetylcholine Receptors Sensitize a MAPK-linked Toxicity Pathway on Prolonged Exposure to $\beta$-Amyloid" J. Biol. Chem, 290, 35, 2015.

International Search Report Issued For PCT Application No. PCT/US2017/046953 dated Nov. 7, 2017.

* cited by examiner (from Wong et al. Nature Neurosci. 5, 633-639, 2002)

(from Ingelsson et al., 2004)

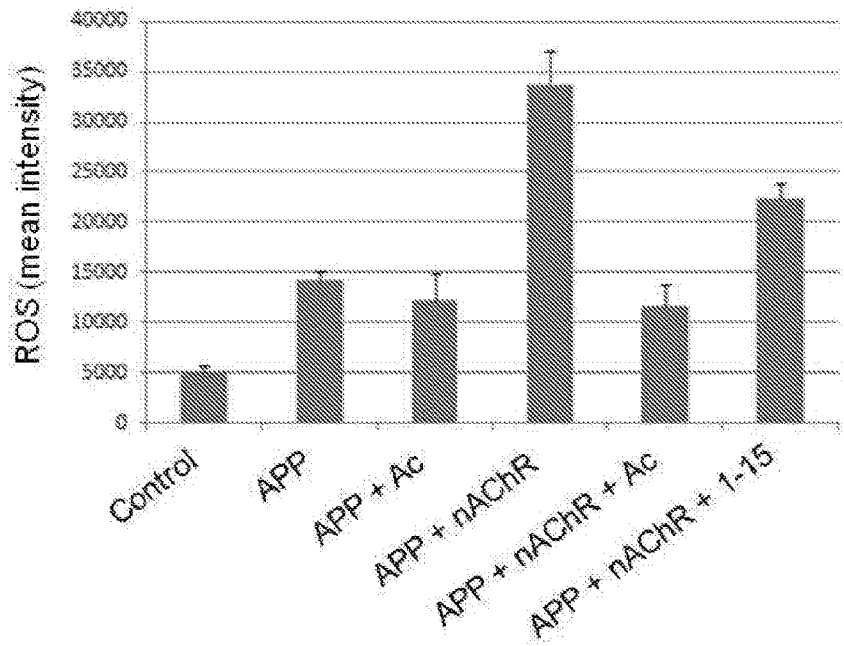
FIG. 8
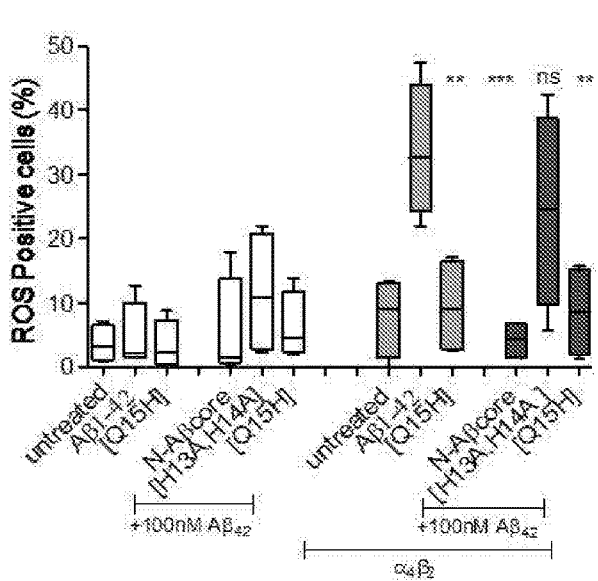 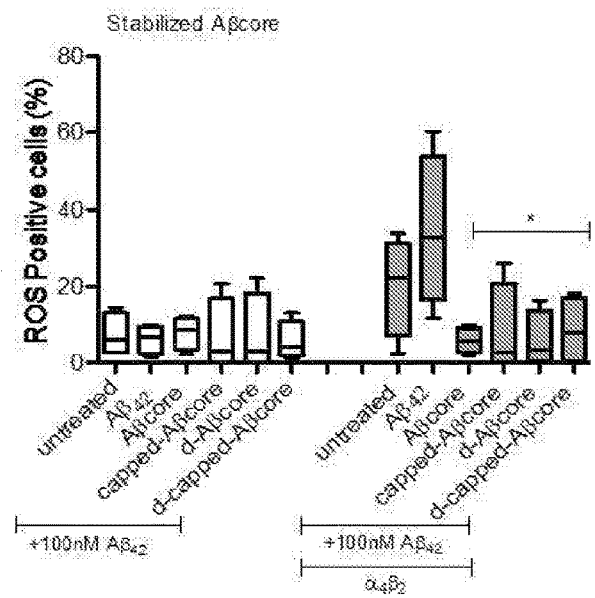
FIG. 9A        FIG. 9B

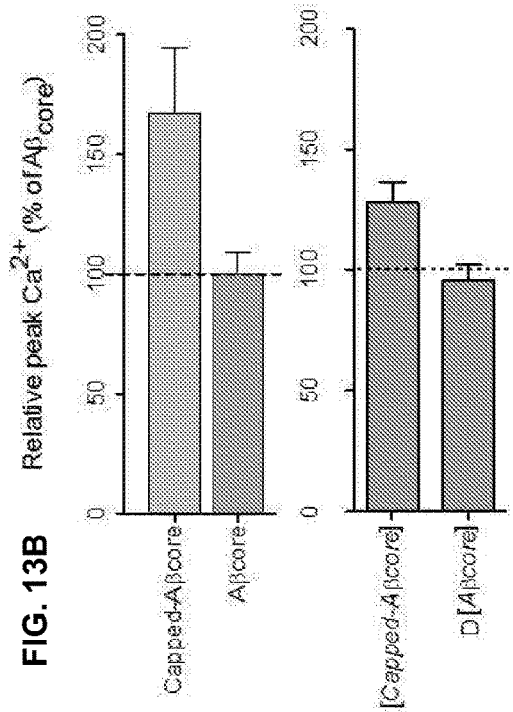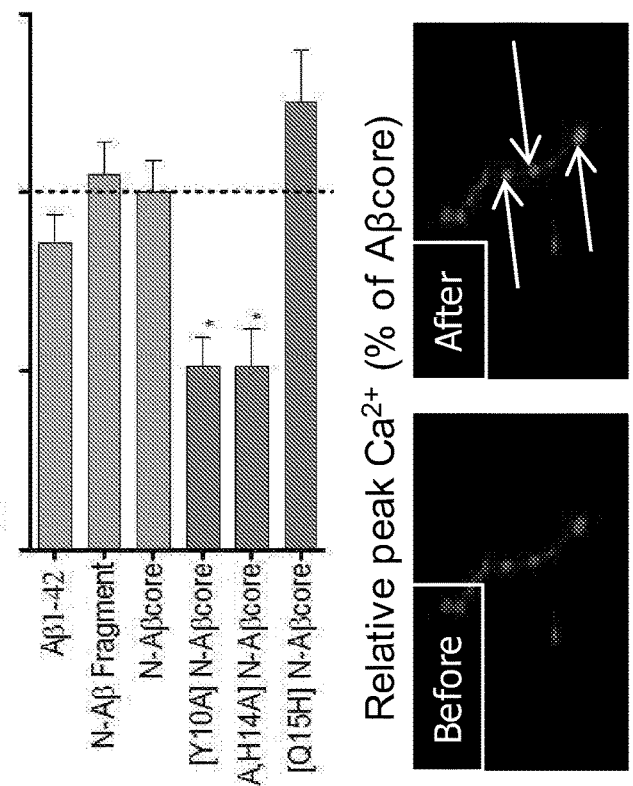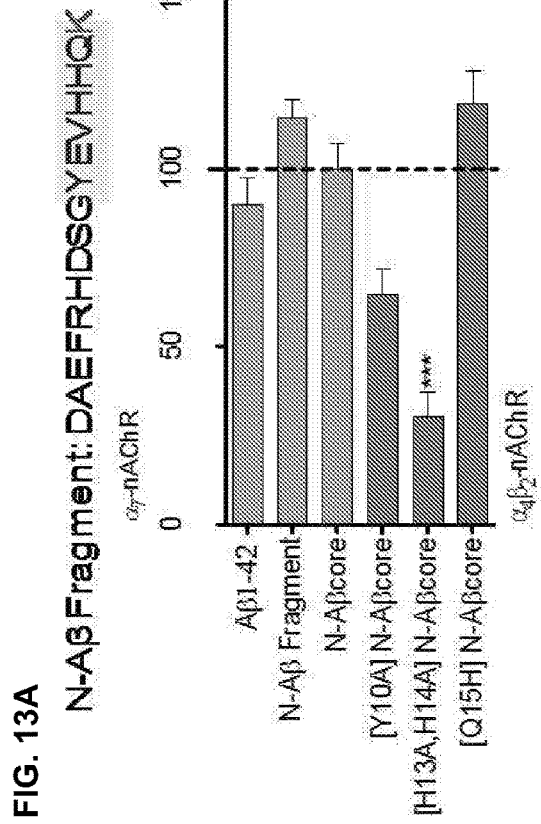
FIG. 13A
FIG. 13B
FIG. 13C

SEQUENCE LISTING

```
<160> NUMBER OF SEQ ID NOS: 63

<210> SEQ ID NO 1
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(6)
<223> OTHER INFORMATION: beta-amyloid core

<400> SEQUENCE: 1

Tyr Glu Val His His Gln
1               5

<210> SEQ ID NO 2
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: N-terminal beta-amyloid  fragment

<400> SEQUENCE: 2

Asp Ala Glu Phe Arg His Asp Ser Gly Tyr Glu Val His His Gln
1               5                   10                  15

<210> SEQ ID NO 3
```

```
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Asp, a conservative substitution thereof, or
      optionally present
<220> FEATURE:
<221> NAME/KEY: MISC_FEATURE
<222> LOCATION: (2)..(2)
<223> OTHER INFORMATION: Ala, a conservative substitution thereof, or
      optionally present
<220> FEATURE:
<221> NAME/KEY: MISC_FEATURE
<222> LOCATION: (3)..(3)
<223> OTHER INFORMATION: Glu, a conservative substitution thereof, or
      optionally present
<220> FEATURE:
<221> NAME/KEY: MISC_FEATURE
<222> LOCATION: (4)..(4)
<223> OTHER INFORMATION: Phe, a conservative substitution thereof, or
      optionally present
<220> FEATURE:
<221> NAME/KEY: MISC_FEATURE
<222> LOCATION: (5)..(5)
<223> OTHER INFORMATION: Arg, a conservative substitution thereof, or
      optionally present
<220> FEATURE:
<221> NAME/KEY: MISC_FEATURE
<222> LOCATION: (6)..(6)
<223> OTHER INFORMATION: His, a conservative substitution thereof, or
      optionally present
<220> FEATURE:
<221> NAME/KEY: MISC_FEATURE
<222> LOCATION: (7)..(7)
<223> OTHER INFORMATION: Asp, a conservative substitution thereof, or
      optionally present
<220> FEATURE:
<221> NAME/KEY: MISC_FEATURE
<222> LOCATION: (8)..(8)
<223> OTHER INFORMATION: Ser, a conservative substitution thereof, or
      optionally present
<220> FEATURE:
<221> NAME/KEY: MISC_FEATURE
<222> LOCATION: (9)..(9)
<223> OTHER INFORMATION: Gly, a conservative substitution thereof, or
      optionally present
<220> FEATURE:
<221> NAME/KEY: MISC_FEATURE
<222> LOCATION: (10)..(15)
<223> OTHER INFORMATION: at least 50% identical to at least a YEVHHQ
      fragment of SEQ ID NO.
<220> FEATURE:
<221> NAME/KEY: MISC_FEATURE
<222> LOCATION: (10)..(10)
<223> OTHER INFORMATION: Tyr or a conservative substitution thereof
<220> FEATURE:
<221> NAME/KEY: MISC_FEATURE
<222> LOCATION: (11)..(11)
<223> OTHER INFORMATION: Glu or a conservative substitution thereof
<220> FEATURE:
<221> NAME/KEY: MISC_FEATURE
<222> LOCATION: (12)..(12)
<223> OTHER INFORMATION: Val or a conservative substitution thereof
<220> FEATURE:
<221> NAME/KEY: MISC_FEATURE
<222> LOCATION: (15)..(15)
<223> OTHER INFORMATION: Gln, His, a conservative substitution thereof,
      or optionally present

<400> SEQUENCE: 3

Xaa Xaa Xaa Xaa Xaa Xaa Xaa Xaa Xaa Xaa Xaa Xaa His His Xaa
1               5                   10                  15
```

```
<210> SEQ ID NO 4
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Phe, Tyr, or Trp
<220> FEATURE:
<221> NAME/KEY: MOD_RES
<222> LOCATION: (1)..(1)
<223> OTHER INFORMATION: acetyl, glycosylation, or -CO-(CH2)nCH3, n=1 to
      10
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MOD_RES
<222> LOCATION: (6)..(6)
<223> OTHER INFORMATION: amidation, reduction or glycosylation

<400> SEQUENCE: 4

Xaa Glu Val His His Gln
1               5

<210> SEQ ID NO 5
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MOD_RES
<222> LOCATION: (6)..(6)
<223> OTHER INFORMATION: amidation, reduction or glycosylation

<400> SEQUENCE: 5

Tyr Xaa Val His His Gln
1               5

<210> SEQ ID NO 6
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
```

```
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (3)..(3)
<223> OTHER INFORMATION: Val, Leu, Ile, or Met
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MOD_RES
<222> LOCATION: (6)..(6)
<223> OTHER INFORMATION: amidation, reduction or glycosylation

<400> SEQUENCE: 6

Tyr Glu Xaa His His Gln
1               5

<210> SEQ ID NO 7
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Asn, or Gln
<220> FEATURE:
<221> NAME/KEY: MOD_RES
<222> LOCATION: (6)..(6)
<223> OTHER INFORMATION: amidation, reduction or glycosylation

<400> SEQUENCE: 7

Tyr Glu Val His His Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Phe, Tyr, or Trp
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
```

```
             to 10
<220> FEATURE:
<221> NAME/KEY: MISC_FEATURE
<222> LOCATION: (2)..(2)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MOD_RES
<222> LOCATION: (6)..(6)
<223> OTHER INFORMATION: amidation, reduction or glycosylation

<400> SEQUENCE: 8

Xaa Xaa Val His His Gln
1               5

<210> SEQ ID NO 9
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Phe, Tyr, or Trp
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (3)..(3)
<223> OTHER INFORMATION: Val, Leu, Ile, or Met
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MOD_RES
<222> LOCATION: (6)..(6)
<223> OTHER INFORMATION: amidation, reduction or glycosylation

<400> SEQUENCE: 9

Xaa Glu Xaa His His Gln
1               5

<210> SEQ ID NO 10
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Phe, Tyr, or Trp
<220> FEATURE:
<221> NAME/KEY: MOD_RES
<222> LOCATION: (1)..(1)
```

```
<223> OTHER INFORMATION: an acetyl, glycosylation, or -CO-(CH2)nCH3, n=1
      to 10
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Asn, or Gln
<220> FEATURE:
<221> NAME/KEY: MOD_RES
<222> LOCATION: (6)..(6)
<223> OTHER INFORMATION: amidation, reduction or glycosylation

<400> SEQUENCE: 10

Xaa Glu Val His His Xaa
1               5

<210> SEQ ID NO 11
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Asp or Glu
<220> FEATURE:
<221> NAME/KEY: MISC_FEATURE
<222> LOCATION: (3)..(3)
<223> OTHER INFORMATION: Val, Leu, Ile, or Met
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MOD_RES
<222> LOCATION: (6)..(6)
<223> OTHER INFORMATION: amidation, reduction or glycosylation

<400> SEQUENCE: 11

Tyr Xaa Xaa His His Gln
1               5

<210> SEQ ID NO 12
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
```

```
<221> NAME/KEY: MISC_FEATURE
<222> LOCATION: (2)..(2)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Asn, or Gln
<220> FEATURE:
<221> NAME/KEY: MOD_RES
<222> LOCATION: (6)..(6)
<223> OTHER INFORMATION: amidation, reduction or glycosylation

<400> SEQUENCE: 12

Tyr Xaa Val His His Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (3)..(3)
<223> OTHER INFORMATION: Val, Leu, Ile, or Met
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Asn, or Gln
<220> FEATURE:
<221> NAME/KEY: MOD_RES
<222> LOCATION: (6)..(6)
<223> OTHER INFORMATION: amidation, reduction or glycosylation

<400> SEQUENCE: 13

Tyr Glu Xaa His His Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Phe, Tyr, or Trp
<220> FEATURE:
```

```
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Asp or Glu
<220> FEATURE:
<221> NAME/KEY: MISC_FEATURE
<222> LOCATION: (3)..(3)
<223> OTHER INFORMATION: Val, Leu, Ile, or Met
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MOD_RES
<222> LOCATION: (6)..(6)
<223> OTHER INFORMATION: amidation, reduction or glycosylation

<400> SEQUENCE: 14

Xaa Xaa Xaa His His Gln
1               5

<210> SEQ ID NO 15
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Phe, Tyr, or Trp
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Asn, or Gln
<220> FEATURE:
<221> NAME/KEY: MOD_RES
<222> LOCATION: (6)..(6)
<223> OTHER INFORMATION: amidation, reduction or glycosylation

<400> SEQUENCE: 15

Xaa Xaa Val His His Xaa
1               5

<210> SEQ ID NO 16
<211> LENGTH: 6
```

```
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Phe, Tyr, or Trp
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (3)..(3)
<223> OTHER INFORMATION: Val, Leu, Ile, or Met
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Asn, or Gln
<220> FEATURE:
<221> NAME/KEY: MOD_RES
<222> LOCATION: (6)..(6)
<223> OTHER INFORMATION: amidation, reduction or glycosylation

<400> SEQUENCE: 16

Xaa Glu Xaa His His Xaa
1               5

<210> SEQ ID NO 17
<211> LENGTH: 6
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Asp or Glu
<220> FEATURE:
<221> NAME/KEY: MISC_FEATURE
<222> LOCATION: (3)..(3)
<223> OTHER INFORMATION: Val, Leu, Ile, or Met
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Asn, or Gln
<220> FEATURE:
<221> NAME/KEY: MOD_RES
<222> LOCATION: (6)..(6)
<223> OTHER INFORMATION: amidation, reduction or glycosylation
```

<400> SEQUENCE: 17

Tyr Xaa Xaa His His Xaa
1               5

<210> SEQ ID NO 18
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 18

Asp Ala Glu Phe Arg His Asp Ser Gly Xaa Glu Val His His Gln
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:

```
<221> NAME/KEY: MOD_RES
<222> LOCATION: (15)..(15)
<223> OTHER INFORMATION: amidation, reduction or glycosylation

<400> SEQUENCE: 19

Asp Ala Glu Phe Arg His Asp Ser Gly Tyr Xaa Val His His Gln
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 20

Asp Ala Glu Phe Arg His Asp Ser Gly Tyr Glu Xaa His His Gln
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
```

```
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 21

Asp Ala Glu Phe Arg His Asp Ser Gly Tyr Glu Val His His Xaa
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 22

Asp Ala Glu Phe Arg His Asp Ser Gly Xaa Xaa Val His His Gln
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (10)..(10)
<223> OTHER INFORMATION: Phe, Tyr, or Trp
<220> FEATURE:
```

```
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 23

Asp Ala Glu Phe Arg His Asp Ser Gly Xaa Glu Xaa His His Gln
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 24

Asp Ala Glu Phe Arg His Asp Ser Gly Xaa Glu Val His His Xaa
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
```

```
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 25

Asp Ala Glu Phe Arg His Asp Ser Gly Tyr Xaa Xaa His His Gln
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 26

Asp Ala Glu Phe Arg His Asp Ser Gly Tyr Xaa Val His His Xaa
1               5                   10                  15
```

```
<210> SEQ ID NO 27
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: Val, Leu, Ile, or Met
<220> FEATURE:
<221> NAME/KEY: MOD_RES
<222> LOCATION: (15)..(15)
<223> OTHER INFORMATION: amidation, reduction or glycosylation

<400> SEQUENCE: 27

Asp Ala Glu Phe Arg His Asp Ser Gly Tyr Glu Xaa His His Xaa
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
```

```
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 28

Asp Ala Glu Phe Arg His Asp Ser Gly Xaa Xaa Xaa His His Gln
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: D-amino Acid and/or N-methylated and/or beta-
      substituted amino acid

<400> SEQUENCE: 29

Asp Ala Glu Phe Arg His Asp Ser Gly Xaa Xaa Val His His Xaa
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
```

```
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 30

Asp Ala Glu Phe Arg His Asp Ser Gly Xaa Glu Xaa His His Xaa
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation
```

<400> SEQUENCE: 31

Asp Ala Glu Phe Arg His Asp Ser Gly Tyr Xaa Xaa His His Xaa
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 32

Asp Ala Glu Phe Xaa His Asp Ser Gly Xaa Xaa Xaa His His Gln
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg

```
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
     substituted amino acid
<220> FEATURE:
<221> NAME/KEY: MOD_RES
<222> LOCATION: (14)..(14)
<223> OTHER INFORMATION: D-amino Acid and/or N-methylated and/or beta-
     substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 33

Asp Ala Glu Phe Xaa His Asp Ser Gly Xaa Xaa Val His His Xaa
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
     to 10
<220> FEATURE:
<221> NAME/KEY: MOD_RES
<222> LOCATION: (4)..(4)
<223> OTHER INFORMATION: D-amino Acid and/or N-methylated and/or beta-
     substituted amino acid
<220> FEATURE:
<221> NAME/KEY: MISC_FEATURE
<222> LOCATION: (5)..(5)
<223> OTHER INFORMATION: Asp or Glu
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
     substituted amino acid
<220> FEATURE:
<221> NAME/KEY: MOD_RES
<222> LOCATION: (14)..(14)
<223> OTHER INFORMATION: D-amino Acid and/or N-methylated and/or beta-
     substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation
```

-continued

<400> SEQUENCE: 34

Asp Ala Glu Phe Xaa His Asp Ser Gly Xaa Glu Xaa His His Xaa
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 35

Asp Ala Glu Phe Xaa His Asp Ser Gly Tyr Xaa Xaa His His Xaa
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-

```
          substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 36

Asp Ala Xaa Phe Xaa His Asp Ser Gly Xaa Xaa Xaa His His Gln
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
```

```
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 37

Asp Ala Xaa Phe Xaa His Asp Ser Gly Xaa Xaa Val His His Xaa
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 38

Asp Ala Xaa Phe Xaa His Asp Ser Gly Xaa Glu Xaa His His Xaa
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: modified beta-amyloid peptide analogue
```

```
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 39

Asp Ala Xaa Phe Xaa His Asp Ser Gly Tyr Xaa Xaa His His Xaa
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Ala, Gly, or Ser
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
```

```
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 40

Asp Xaa Xaa Phe Xaa His Asp Ser Gly Xaa Xaa Xaa His His Gln
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Ala, Gly, or Ser
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
```

```
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 41

Asp Xaa Xaa Phe Xaa His Asp Ser Gly Xaa Xaa Val His His Xaa
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
     to 10
<220> FEATURE:
<221> NAME/KEY: MISC_FEATURE
<222> LOCATION: (2)..(2)
<223> OTHER INFORMATION: Ala, Gly, or Ser
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
     substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
     substituted amino acid
<220> FEATURE:
<221> NAME/KEY: MOD_RES
<222> LOCATION: (14)..(14)
<223> OTHER INFORMATION: D-amino Acid and/or N-methylated and/or beta-
     substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 42

Asp Xaa Xaa Phe Xaa His Asp Ser Gly Xaa Glu Xaa His His Xaa
1               5                   10                  15

<210> SEQ ID NO 43
<211> LENGTH: 15
<212> TYPE: PRT
```

```
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Ala, Gly, or Ser
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 43

Asp Xaa Xaa Phe Xaa His Asp Ser Gly Tyr Xaa Xaa His His Xaa
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Asp or Glu
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Ala, Gly, or Ser
<220> FEATURE:
<221> NAME/KEY: MISC_FEATURE
```

```
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 44

Xaa Xaa Xaa Phe Xaa His Asp Ser Gly Xaa Xaa Xaa His His Gln
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Asp or Glu
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Ala, Gly, or Ser
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (10)..(10)
```

```
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 45

Xaa Xaa Xaa Phe Xaa His Asp Ser Gly Xaa Xaa Val His His Xaa
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Asp or Glu
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: Ala, Gly, or Ser
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
``` substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 46

Xaa Xaa Xaa Phe Xaa His Asp Ser Gly Xaa Glu Xaa His His Xaa
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MISC_FEATURE
<222> LOCATION: (1)..(1)
<223> OTHER INFORMATION: Asp or Glu
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
    to 10
<220> FEATURE:
<221> NAME/KEY: MISC_FEATURE
<222> LOCATION: (2)..(2)
<223> OTHER INFORMATION: Ala, Gly, or Ser
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 47

Xaa Xaa Xaa Phe Xaa His Asp Ser Gly Tyr Xaa Xaa His His Xaa
1               5                   10                  15

```
<210> SEQ ID NO 48
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 48

Asp Ala Glu Phe Arg Xaa Asp Ser Gly Xaa Glu Val His His Gln
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (4)..(4)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
```

```
       substituted amino acid
<220> FEATURE:
<221> NAME/KEY: MOD_RES
<222> LOCATION: (14)..(14)
<223> OTHER INFORMATION: D-amino Acid and/or N-methylated and/or beta-
       substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 49

Asp Ala Glu Phe Arg Xaa Asp Ser Gly Xaa Xaa Val His His Gln
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
       to 10
<220> FEATURE:
<221> NAME/KEY: MOD_RES
<222> LOCATION: (4)..(4)
<223> OTHER INFORMATION: D-amino Acid and/or N-methylated and/or beta-
       substituted amino acid
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
       substituted amino acid
<220> FEATURE:
<221> NAME/KEY: MOD_RES
<222> LOCATION: (14)..(14)
<223> OTHER INFORMATION: D-amino Acid and/or N-methylated and/or beta-
       substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 50

Asp Ala Glu Phe Arg Xaa Asp Ser Gly Xaa Glu Xaa His His Xaa
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
```

<223> OTHER INFORMATION: an acetyl, glycosylation, or -CO-(CH2)nCH3, n=1 to 10
<220> FEATURE:
<221> NAME/KEY: MOD_RES
<222> LOCATION: (4)..(4)
<223> OTHER INFORMATION: D-amino Acid and/or N-methylated and/or beta-substituted amino acid
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-substituted amino acid
<220> FEATURE:
<221> NAME/KEY: MOD_RES
<222> LOCATION: (14)..(14)
<223> OTHER INFORMATION: D-amino Acid and/or N-methylated and/or beta-substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 51

Asp Ala Glu Phe Arg Xaa Asp Ser Gly Tyr Xaa Xaa His His Xaa
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1 to 10
<220> FEATURE:
<221> NAME/KEY: MOD_RES
<222> LOCATION: (5)..(5)
<223> OTHER INFORMATION: D-amino Acid and/or N-methylated and/or beta-substituted amino acid
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MISC_FEATURE
<222> LOCATION: (7)..(7)
<223> OTHER INFORMATION: Asp or Glu
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MOD_RES
<222> LOCATION: (13)..(13)
<223> OTHER INFORMATION: D-amino Acid and/or N-methylated and/or beta-substituted amino acid
<220> FEATURE:
<221> NAME/KEY: MOD_RES

```
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 52

Asp Ala Glu Phe Arg Xaa Xaa Ser Gly Xaa Glu Val His His Gln
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MISC_FEATURE
<222> LOCATION: (7)..(7)
<223> OTHER INFORMATION: Asp or Glu
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 53

Asp Ala Glu Phe Arg Xaa Xaa Ser Gly Xaa Xaa Val His His Gln
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
```

```
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MISC_FEATURE
<222> LOCATION: (7)..(7)
<223> OTHER INFORMATION: Asp or Glu
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 54

Asp Ala Glu Phe Arg Xaa Xaa Ser Gly Xaa Glu Xaa His His Xaa
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (5)..(5)
<223> OTHER INFORMATION: D-amino Acid and/or N-methylated and/or beta-
      substituted amino acid
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MISC_FEATURE
<222> LOCATION: (7)..(7)
<223> OTHER INFORMATION: Asp or Glu
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
```

```
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 55

Asp Ala Glu Phe Arg Xaa Xaa Ser Gly Tyr Xaa Xaa His His Xaa
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MOD_RES
<222> LOCATION: (6)..(6)
<223> OTHER INFORMATION: D-amino Acid and/or N-methylated and/or beta-
      substituted amino acid
<220> FEATURE:
<221> NAME/KEY: MISC_FEATURE
<222> LOCATION: (7)..(7)
<223> OTHER INFORMATION: Asp or Glu
<220> FEATURE:
<221> NAME/KEY: MISC_FEATURE
<222> LOCATION: (8)..(8)
<223> OTHER INFORMATION: Ala, Gly, or Ser
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 56

Asp Ala Glu Phe Arg Xaa Xaa Xaa Gly Xaa Glu Val His His Gln
1               5                   10                  15

<210> SEQ ID NO 57
<211> LENGTH: 15
<212> TYPE: PRT
```

```
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MOD_RES
<222> LOCATION: (6)..(6)
<223> OTHER INFORMATION: D-amino Acid and/or N-methylated and/or beta-
      substituted amino acid
<220> FEATURE:
<221> NAME/KEY: MISC_FEATURE
<222> LOCATION: (7)..(7)
<223> OTHER INFORMATION: Asp or Glu
<220> FEATURE:
<221> NAME/KEY: MISC_FEATURE
<222> LOCATION: (8)..(8)
<223> OTHER INFORMATION: Ala, Gly, or Ser
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MOD_RES
<222> LOCATION: (15)..(15)
<223> OTHER INFORMATION: amidation, reduction or glycosylation

<400> SEQUENCE: 57

Asp Ala Glu Phe Arg Xaa Xaa Xaa Gly Xaa Xaa Val His His Gln
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MOD_RES
<222> LOCATION: (6)..(6)
<223> OTHER INFORMATION: D-amino Acid and/or N-methylated and/or beta-
      substituted amino acid
<220> FEATURE:
<221> NAME/KEY: MISC_FEATURE
<222> LOCATION: (7)..(7)
<223> OTHER INFORMATION: Asp or Glu
<220> FEATURE:
```

```
<221> NAME/KEY: MISC_FEATURE
<222> LOCATION: (8)..(8)
<223> OTHER INFORMATION: Ala, Gly, or Ser
<220> FEATURE:
<221> NAME/KEY: MISC_FEATURE
<222> LOCATION: (10)..(10)
<223> OTHER INFORMATION: Phe, Tyr, or Trp
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 58

Asp Ala Glu Phe Arg Xaa Xaa Xaa Gly Xaa Glu Xaa His His Xaa
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (6)..(6)
<223> OTHER INFORMATION: His, Lys, or Arg
<220> FEATURE:
<221> NAME/KEY: MOD_RES
<222> LOCATION: (6)..(6)
<223> OTHER INFORMATION: D-amino Acid and/or N-methylated and/or beta-
      substituted amino acid
<220> FEATURE:
<221> NAME/KEY: MISC_FEATURE
<222> LOCATION: (7)..(7)
<223> OTHER INFORMATION: Asp or Glu
<220> FEATURE:
<221> NAME/KEY: MISC_FEATURE
<222> LOCATION: (8)..(8)
<223> OTHER INFORMATION: Ala, Gly, or Ser
<220> FEATURE:
<221> NAME/KEY: MISC_FEATURE
<222> LOCATION: (11)..(11)
<223> OTHER INFORMATION: Asp or Glu
<220> FEATURE:
<221> NAME/KEY: MISC_FEATURE
<222> LOCATION: (12)..(12)
<223> OTHER INFORMATION: Val, Leu, Ile, or Met
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
```

```
<222> LOCATION: (14)..(14)
<223> OTHER INFORMATION: D-amino Acid and/or N-methylated and/or beta-
      substituted amino acid
<220> FEATURE:
<221> NAME/KEY: MISC_FEATURE
<222> LOCATION: (15)..(15)
<223> OTHER INFORMATION: His, Asn, or Gln
<220> FEATURE:
<221> NAME/KEY: MOD_RES
<222> LOCATION: (15)..(15)
<223> OTHER INFORMATION: amidation, reduction or glycosylation

<400> SEQUENCE: 59

Asp Ala Glu Phe Arg Xaa Xaa Xaa Gly Tyr Xaa Xaa His His Xaa
1               5                   10                  15

<210> SEQ ID NO 60
<211> LENGTH: 14
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (5)..(5)
<223> OTHER INFORMATION: His, Lys, or Arg
<220> FEATURE:
<221> NAME/KEY: MISC_FEATURE
<222> LOCATION: (6)..(6)
<223> OTHER INFORMATION: Asp or Glu
<220> FEATURE:
<221> NAME/KEY: MISC_FEATURE
<222> LOCATION: (7)..(7)
<223> OTHER INFORMATION: Ala, Gly, or Ser
<220> FEATURE:
<221> NAME/KEY: MISC_FEATURE
<222> LOCATION: (8)..(8)
<223> OTHER INFORMATION: Ala, Gly, or Ser
<220> FEATURE:
<221> NAME/KEY: MISC_FEATURE
<222> LOCATION: (9)..(9)
<223> OTHER INFORMATION: Phe, Tyr, or Trp
<220> FEATURE:
<221> NAME/KEY: MOD_RES
<222> LOCATION: (9)..(9)
<223> OTHER INFORMATION: D-amino Acid and/or N-methylated and/or beta-
      substituted amino acid
<220> FEATURE:
<221> NAME/KEY: MOD_RES
<222> LOCATION: (12)..(12)
<223> OTHER INFORMATION: D-amino Acid and/or N-methylated and/or beta-
      substituted amino acid
<220> FEATURE:
<221> NAME/KEY: MOD_RES
<222> LOCATION: (13)..(13)
<223> OTHER INFORMATION: D-amino Acid and/or N-methylated and/or beta-
      substituted amino acid
<220> FEATURE:
<221> NAME/KEY: MOD_RES
<222> LOCATION: (14)..(14)
<223> OTHER INFORMATION: amidation, reduction or glycosylation

<400> SEQUENCE: 60

Ala Glu Phe Arg Xaa Xaa Xaa Xaa Xaa Glu Val His His Gln
1               5                   10

<210> SEQ ID NO 61
<211> LENGTH: 13
<212> TYPE: PRT
<213> ORGANISM: Artificial Sequence
```

```
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (4)..(4)
<223> OTHER INFORMATION: His, Lys, or Arg
<220> FEATURE:
<221> NAME/KEY: MISC_FEATURE
<222> LOCATION: (5)..(5)
<223> OTHER INFORMATION: Asp or Glu
<220> FEATURE:
<221> NAME/KEY: MISC_FEATURE
<222> LOCATION: (6)..(6)
<223> OTHER INFORMATION: Ala, Gly, or Ser
<220> FEATURE:
<221> NAME/KEY: MISC_FEATURE
<222> LOCATION: (7)..(7)
<223> OTHER INFORMATION: Ala, Gly, or Ser
<220> FEATURE:
<221> NAME/KEY: MISC_FEATURE
<222> LOCATION: (8)..(8)
<223> OTHER INFORMATION: Phe, Tyr, or Trp
<220> FEATURE:
<221> NAME/KEY: MOD_RES
<222> LOCATION: (8)..(8)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (9)..(9)
<223> OTHER INFORMATION: Asp or Glu
<220> FEATURE:
<221> NAME/KEY: MOD_RES
<222> LOCATION: (11)..(11)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (12)..(12)
<223> OTHER INFORMATION: an acetyl, glycosylation, or -CO-(CH2)nCH3, n=1
      to 10
<220> FEATURE:
<221> NAME/KEY: MOD_RES
<222> LOCATION: (13)..(13)
<223> OTHER INFORMATION: amidation, reduction or glycosylation

<400> SEQUENCE: 61

Glu Phe Arg Xaa Xaa Xaa Xaa Xaa Xaa Val His His Gln
1               5                   10

<210> SEQ ID NO 62
<211> LENGTH: 12
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (3)..(3)
<223> OTHER INFORMATION: His, Lys, or Arg
<220> FEATURE:
<221> NAME/KEY: MISC_FEATURE
<222> LOCATION: (4)..(4)
<223> OTHER INFORMATION: Asp or Glu
<220> FEATURE:
<221> NAME/KEY: MISC_FEATURE
<222> LOCATION: (5)..(5)
```

```
<223> OTHER INFORMATION: Ala, Gly, or Ser
<220> FEATURE:
<221> NAME/KEY: MISC_FEATURE
<222> LOCATION: (6)..(6)
<223> OTHER INFORMATION: Ala, Gly, or Ser
<220> FEATURE:
<221> NAME/KEY: MISC_FEATURE
<222> LOCATION: (7)..(7)
<223> OTHER INFORMATION: Phe, Tyr, or Trp
<220> FEATURE:
<221> NAME/KEY: MOD_RES
<222> LOCATION: (7)..(7)
<223> OTHER INFORMATION: D-amino Acid and/or N-methylated and/or beta-
      substituted amino acid
<220> FEATURE:
<221> NAME/KEY: MISC_FEATURE
<222> LOCATION: (9)..(9)
<223> OTHER INFORMATION: Val, Leu, Ile, or Met
<220> FEATURE:
<221> NAME/KEY: MOD_RES
<222> LOCATION: (10)..(10)
<223> OTHER INFORMATION: D-amino Acid and/or N-methylated and/or beta-
      substituted amino acid
<220> FEATURE:
<221> NAME/KEY: MOD_RES
<222> LOCATION: (11)..(11)
<223> OTHER INFORMATION: D-amino Acid and/or N-methylated and/or beta-
      substituted amino acid
<220> FEATURE:
<221> NAME/KEY: MISC_FEATURE
<222> LOCATION: (12)..(12)
<223> OTHER INFORMATION: His, Asn, or Gln
<220> FEATURE:
<221> NAME/KEY: MOD_RES
<222> LOCATION: (12)..(12)
<223> OTHER INFORMATION: amidation, reduction or glycosylation

<400> SEQUENCE: 62

Phe Arg Xaa Xaa Xaa Xaa Xaa Glu Xaa His His Xaa
1               5                   10

<210> SEQ ID NO 63
<211> LENGTH: 11
<212> TYPE: PRT
<213> ORGANISM: Artificial Sequence
<220> FEATURE:
<223> OTHER INFORMATION: modified beta-amyloid peptide analogue
<220> FEATURE:
<221> NAME/KEY: MOD_RES
<222> LOCATION: (1)..(1)
<223> OTHER INFORMATION: an acetyl, glycosylation, or -CO-(CH2)nCH3, n=1
      to 10
<220> FEATURE:
<221> NAME/KEY: MISC_FEATURE
<222> LOCATION: (2)..(2)
<223> OTHER INFORMATION: His, Lys, or Arg
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MISC_FEATURE
<222> LOCATION: (4)..(4)
<223> OTHER INFORMATION: Ala, Gly, or Ser
<220> FEATURE:
<221> NAME/KEY: MISC_FEATURE
<222> LOCATION: (5)..(5)
<223> OTHER INFORMATION: Ala, Gly, or Ser
<220> FEATURE:
<221> NAME/KEY: MOD_RES
<222> LOCATION: (6)..(6)
<223> OTHER INFORMATION: D-amino Acid and/or N-methylated and/or beta-
      substituted amino acid
<220> FEATURE:
<221> NAME/KEY: MISC_FEATURE
<222> LOCATION: (7)..(7)
<223> OTHER INFORMATION: Asp or Glu
```

```
<220> FEATURE:
<221> NAME/KEY: MISC_FEATURE
<222> LOCATION: (8)..(8)
<223> OTHER INFORMATION: Val, Leu, Ile, or Met
<220> FEATURE:
<221> NAME/KEY: MOD_RES
<222> LOCATION: (9)..(9)
<223> OTHER INFORMATION: D-amino Acid and/or N-methylated and/or beta-
      substituted amino acid
<220> FEATURE:
<221> NAME/KEY: MOD_RES
<222> LOCATION: (10)..(10)
<223> OTHER INFORMATION: D-amino Acid and/or N-methylated and/or beta-
      substituted amino acid
<220> FEATURE:
<221> NAME/KEY: MISC_FEATURE
<222> LOCATION: (11)..(11)
<223> OTHER INFORMATION: His, Asn, or Gln
<220> FEATURE:
<221> NAME/KEY: MOD_RES
<222> LOCATION: (11)..(11)
<223> OTHER INFORMATION: amidation, reduction or glycosylation

<400> SEQUENCE: 63

Arg Xaa Xaa Xaa Xaa Tyr Xaa Xaa His His Xaa
1               5                   10
```

NEUROPROTECTIVE BETA AMYLOID CORE PEPTIDES AND PEPTIDOMIMETIC DERIVATIVES

CROSS-REFERENCES TO RELATED APPLICATIONS

This application is a 371 and claims benefit of PCT/US2017/046953 filed Aug. 15, 2017, which claims benefit of U.S. Provisional Application No. 62/377,556 filed Aug. 20, 2016, the specification(s) of which is/are incorporated herein in their entirety by reference.

FIELD OF THE INVENTION

The present invention relates to stabilized derivatives and peptidomimetics of a core amino acid sequence in β-amyloid (Aβ) for treatment and prevention of β-amyloid-induced toxicity.

REFERENCE TO SEQUENCE LISTING

Applicant asserts that the information recorded in the form of an Annex C/ST.25 text file submitted under Rule 13ter.1(a), entitled UNIA_16_46_PCT_Sequence_Listing_ST25.txt, is identical to that forming part of the international application as filed. The content of the sequence listing is incorporated herein by reference in its entirety.

BACKGROUND OF THE INVENTION

Alzheimer's disease (AD) is a progressive neurodegenerative disorders leading to dementia. It is a progressive neurodegenerative disease having symptoms such by memory loss, cognitive decline, and language dysfunction. AD is characterized by various pathological hallmarks including extracellular plaques composed primarily of β-arnyloid (Aβ), intracellular neurofibrillary tangles formed from hyperphosphorylated tau, synaptic loss, local inflammation, and neurodecieneration in brain regions critical for memory processes. The onset of AD is best correlated with increased levels of Aβ. There is a substantial body of research to indicate that Aβ is one of the key triggers of the disease, leading to loss of synapses (the points of communication between nerve cells) and nerve cells (lines of communication) in regions of the brain involved with memory and cognition, both of which eventually fail in AD.

The β-amyloid is a small, toxic peptide cleaved from the amyloid precursor protein (APP). APP is a single spanning transmembrane (TM) protein whose function is still largely unknown but is believed to be involved in neurite outgrowth, neuronal protein trafficking, signal transduction, cell adhesion, and calcium metabolism. As shown in FIG. 2, the 15-16 amino acid N-terminal Aβ fragment ("N-Aβ fragment") is produced via an α-secretase-linked pathway (α- and β-secretases) and is present at significant levels in cerebrospinal fluid (CSF).

The plaques are primarily composed of fibrillar β-amyloid, but the noted development of synaptic impairment is best correlated with the level of soluble Aβ early in AD, followed by the accumulation of neurofibrillary tangles. In the absence of disease, the production of Aβ from synapses and the high rate of turnover of soluble Aβ raise the possibility that the peptide can function as a neuromodulator under normal physiological conditions. Later, as Aβ accumulates, its action may then become disruptive, leading to compromised synaptic signaling.

Currently approved treatments for Alzheimer's disease (and related dementias) are limited to transient relief of early symptoms (e.g. short-term memory deficit) with no significant impact on the state or progression of the disease, particularly neurodegeneration. In addition, the current treatments are only effective in a portion of the population of individuals with Alzheimer's disease and only for a limited period of time. To date, there is no effective cure for the disease, but identifying and characterizing the cellular mechanisms underlying AD will potentially elucidate a target pathway for potential treatment.

Lawrence et al. has recently shown that at tow concentrations (picomolar (pM)-nanomolar ((nM)), the N-terminal Aβ fragment is nearly twice as effective as full-length Aβ as a neuromodulator, stimulating receptor-linked increases in $Ca^{2+}$, enhancing long-term potentiation (LTP) and enhancing contextual fear conditioning (Lawrence et al., J. Neuroscience, 34: 14210-14218, 2014). The activity of the N-Aβ fragment was localized to a core hexapeptide sequence within the N-Aβ fragment ("Aβ core sequence"). The presence of high-affinity nicotinic acetylcholine receptors (nAChRs) was found to sensitize neurons to Aβ-induced toxic effects (Arora et al., J. Biol. Chem, 288: 11175-11190, 2013). Models show that application of high concentrations (μM levels) of Aβ induces apoptosis in the absence of nAChRs.

As will be described herein, the present invention focuses on the potential activity of the core sequence in neurotoxicity and synaptotoxicity models. Without wishing to limit the invention to a particular theory or mechanism, it is proposed that nAChRs sensitize Aβ-induced neuronal death by intersecting with a common neurotoxicity pathway involving distinct Aβ target receptor(s). The N-terminal Aβ fragment were found to inhibit this neurotoxicity and reverse inhibition of synaptic dynamics triggered by full-length Aβ, suggesting the possibility of neuroprotection.

SUMMARY OF THE INVENTION

The inventors have discovered a core six amino acid sequence in beta amyloid, Tyrosine-Glutamate-Valine-Histidine-Histidine-Glutamine (YEVHHQ, SEQ No. 1, single letter abbreviation), which may be referred to herein as "core" or "Aβ core". Unexpectedly, this core demonstrates potent and highly effective neuroprotective activity against the toxic action of beta amyloid in killing synapses and nerve cells. The present invention transforms this peptide sequence into a stabilized derivative and/or a peptidomimetic (non-peptide small molecule), which may be used as a therapeutic for treatment of Alzheimer's disease and related dementias.

The subject disclosure is directed to active stabilized peptide derivatives (biologic) and/or peptidomimetics (synthetic) derived from the Aβ core sequence. Without wishing to limit the invention to any theory or mechanism, it is believed that the technical feature of the present invention advantageously overcomes the issues pertaining to the delivery of peptides into the brain, thereby allowing protection against synaptic dysfunction and neurodegeneration in the brain arising from (β-amyloid toxicity, such as those associated with Alzheimer's disease and other related neurodegenerative disorders. The present invention is a unique approach that is qualitatively better and more effective, and that it benefits a larger portion of the population. More importantly, the present invention has the potential to significantly slow down or arrest the neurodegenerative process. None of the presently known prior references or work has the unique inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which:

FIG. 5A shows oxidative stress (ROS, reactive oxygen species) and FIG. 5B shows DNA fragmentation in apoptosis. Treatment is with 100 nM N-Aβcore after 0-, 1-, 2-day treatment of 100 nM Aβ1-42 in the presence α4β2-nAChR (n=5 experiments).

FIG. 6A shows oxidative stress (ROS) and FIG. 6B shows DNA fragmentation in apoptosis. Treatment of 100 nm or 1 μM N-Aβ core or N-Aβ fragment is alone and in combination with 1 μM Aβ1-42 (n=5 experiments). Note that in the absence of nAChRs, μM concentrations of Aβ1-42 are required to increase ROS, Co-treatments with Aβ1-42 are represented by closed (grey) bars.

FIG. 7A shows 5-day and FIG. 7B shows 10-day daily treatments with 1 μM Aβ1-42, 1 μM N-Aβ fragment, or 1 μM N-Aβcore and combination treatments of 1 μM Aβ1-42 and 1 μN-Aβ fragment or 1 μM N-Aβcore (n=4 experiments).

FIG. 8 shows that the N-Aβ fragment protects against cellular toxicity (oxidative stress: ROS) induced by endogenously produced Aβ (from transfected APP).

FIGS. 9A-9B show the requirement for the histidine residues in the N-Aβ core sequence and the stabilization of the N-Aβ core sequence by N-acetylation and C-amidation Ira the protection against Aβ-induced cellular toxicity. FIG. 9A shows co-treatment of 100 nM Aβ1-42 with 100 nM [H13A, H13A] N-Aβcore or 100 nM [Q15H] N-Aβcore (n=4 experiments). FIG. 9B shows daily co-treatment with 100 nM Aβ1-42 and 100 nM capped-Aβcore, D-[Aβcore] or Capped-D-[Aβcore] reduces ROS. Mock-transfected cells are represented by open bars; α4β2-nAChR-transfected cells are represented by closed (grey) bars.

FIG. 10A shows normalized cell counts in a model neuronal cell lines (NG108-15 cells) with, or without, α4β2-nAChRs treated dally with 100 nM Aβ1-42, N-Aβ fragment or N-Aβcore alone, or combination treatments with Aβ1-42 and N-Aβ fragment or N-Aβcore over 7 days (n=4 experiments). FIG. 10B shows cell counts in primary hippocampal cell cultures (mouse primary hippocampal neurons) treated daily with 1 μM Aβ1-42, N-Aβ fragment or N-Aβcore alone, or combination deity treatments with Aβ1-42 and N-Aβ fragment or N-Aβcore for 10 days (n=4 experiments).

FIGS. 13A-13C show structure-activity analysis of the N-Aβ core sequence, peptide stabilization and comparison to kinetics of Aβ. In FIG. 13A, the top graph shows average peak $Ca^{2+}$ responses in varicosities of cells expressing α7-nAChRs to 100 nM Aβ1-42 (n=44), N-Aβcore (n=70), N-Aβ fragment (n=178), [Y10A] N-Aβcore (n=14), [H13A, H14A] N-Aβcore. (n=19), and [Q15H] Nβcore (n=33). The bottom gaph shows average peak $Ca^{2+}$ responses in varicosities of cells expressing α4β2-nAChRs to 100 nM Aβ1-42 (n=36), N-Aβcore (n=32), N-Aβ fragment (n=35), [Y10] N-Aβcore (n=21), [H13A, H14A] N-βcore (n=19), and [Q15H] N-Aβcore (n=29). Averaged data are means±SEM and dashed lines indicate the baseline (background) and average maximal responses of N-Aβcore. *p<0.05 and ***p<0.0001. FIG. 13B, top, shows average peak. $Ca^{2+}$ responses in varicosities of cells expressing α4β2-nAChRs to 100 nM N-Aβcore (n=51) and "capped"-Aβcore (n=23). Protection of N-Aβcore via N-terminal acetylation and C-terminal amidation (capped) retains activity compared to N-Aβcore. FIG. 13B, bottom, shows peak responses to 100 nM D-[Aβcore] (n=57) and Capped-D[Aβcore] (n=65). Enantiomer conversion and stabilization of N-Aβcore retains activity. Averaged data are mean±S.E.M, and dashed lines indicate the average maximal responses of N-Aβcore. FIG. 13C shows average $Ca^{2+}$ responses ($F/F_0$) in varicosities of NG108-15 cells expressing α4β2-nAChRs to 100 nM N-Aβcore (n=33) 100 nM N-Aβ Fragment (n=17) and 100 nM $Aβ_{1-42}$ (n=40) over 13 minutes of treatment. Averaged data are means±SEM and n represents the total number of varicosities examined FIGS. 14A-14B N-Aβ core sequence rescue of DNA fragmentation in apoptosis (TUNEL staining) with or without nAChRs in the differentiated neuronal cell line (NG108-15).

DETAILED DESCRIPTION OF THE INVENTION

Figure 1A:
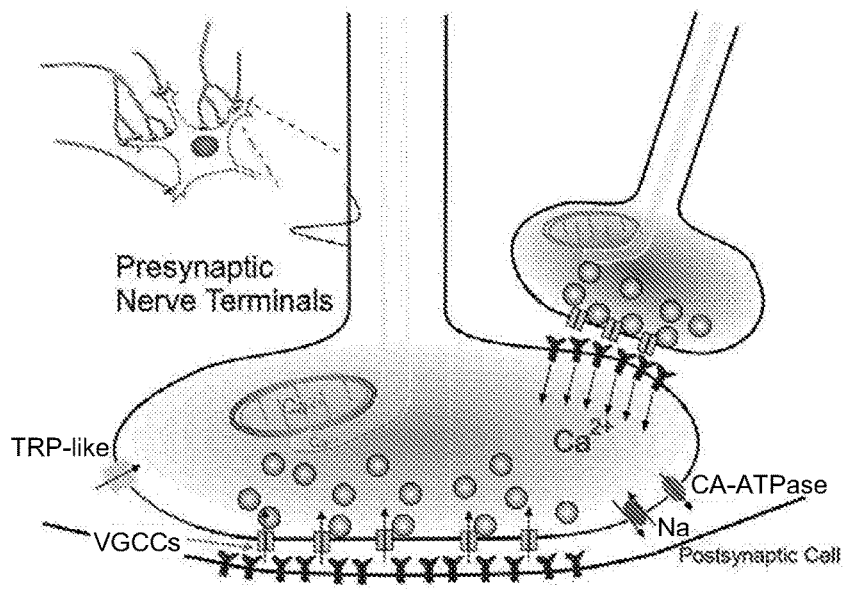
FIG. 1A shows a diagrammatic representation of presynaptic regulation occurring via nerve activity and/or resident receptors.

As the neuroprotective potential of the N-terminal Aβ fragment to inhibit and for reverse cellular neurotoxicity and synaptic dysfunction triggered by full-length Aβ through target receptors was shown to reside in the N-Aβcore, this present invention focuses on derivation and/or stabilization of the core sequence and analogues thereof.

As used herein, the "natural amino acids" refers to the twenty amino acids that are found in nature, i.e. occur naturally. The natural amino acids are as follows: alanine, arginine, glycine, asparagine, aspartic acid, cysteine, glutamine, glutamic acid, serine, threonine, histidine, lysine, methionine, proline, valine, isoleucine, leucine, tyrosine, tryptophan, and phenylalanine. This application adheres to the IUPAC rules of standard abbreviations for amino acids.

As used herein, the "unnatural amino acids" refers to amino acids that are not naturally encoded or found in the genetic code of any organisms. Typically, the unnatural amino acids are different from the twenty naturally occurring amino acids in their side chain functionality.

A "peptide" is defined as an amino acid sequence from three amino acids to about 700 amino acids in length. As used herein, a "peptide analogue" includes allelic variants; fragments; derivatives; substitution, deletion, insertion variants, fusion polypeptides and orthologs. Each amino acid of each such related peptide analogue may be either natural or unnatural of the "D" or "L" configuration which corresponds to the stereochemical designation "S" and "R," respectively, as defined in the RS system of Cahn et al., (Pure Applied Chemistry, 45:11-30 (1974), and references cited therein). As known to one of ordinary skill in the art, only L-amino acids are manufactured in cells and incorporated into proteins. As used herein, the letter "D" preceding any three-letter abbreviation for an amino acid, e.g. as in "D-His", denotes the D-form of the amino acid, and a lack thereof refers to the L-form.

As defined herein, the term "agonist" refers to compound that enhances a response. The agonist binds to the same site as the endogenous compound and produces the same type of signal, usually of equal or greater magnitude than the endogenous agent. As defined herein, the term "antagonist" refers to compound that binds to the same site as the endogenous compound and diminishes or blocks the signal generated by the endogenous agent.

As used herein, for each amino acid, the amino acid residue of the peptide analogue may be preserved, which is defined as keeping said amino acid in the sequence. However, preserved does not imply unmodified. The amino acid may be preserved, but can also be modified. For example, a Histidine residue may be modified to a D-His, N-alkylated His (e.g. N-methylated His), or a β-substituted His.

In contrast, a conservative substitution, as known to one of ordinary skill in the art, refers to a complete replacement of an amino acid residue with a different residue having similar biochemical characteristics, such as size, charge, polarity, etc. For instance, the aromatic Tyrosine may be conservatively substituted with aromatic phenylalanine, or basic Arginine may be conservatively substituted with basic Lysine. TABLE 1A and 1B show non-limiting examples of conservative amino add substitutions.

TABLE 1A

| Original Residue | Conservative Substitution |
| --- | --- |
| Ala (A) | Cys, Gly, Ser, Thr, Val |
| Arg (R) | Asn, Gln, Glu, His, Lys |
| Asn (N) | Arg, Asp, Gln, Glu, His, Lys, Ser, Thr |
| Asp (D) | Asn, Gln, Glu, Ser |
| Cys (C) | Ala, Ser |
| Gln (Q) | Arg, Asn, Asp, Glu, His, Lys, Met, Ser |
| Glu (E) | Arg, Asn, Asp, Gln, His, Lys, Ser |
| Gly (G) | Ala, Ser, Glu, Asp |
| Ile (I) | Leu, Met, Phe, Val |
| Leu (L) | Ile, Met, Phe, Val |
| Lys (K) | Arg, Asn, Gln, Glu, Ser |
| Met (M) | Gln, Ile, Leu, Phe, Val |
| Phe (F) | Ile, Leu, Met, Trp, Tyr |
| Pro (P) | None |
| Ser (S) | Ala, Asn, Asp, Gln, Glu, Gly, Lys, Thr |
| Thr (T) | Ala, Asn, Ser, Val |
| Trp (W) | Phe, Tyr |
| Tyr (Y) | His, Phe, Trp, |
| Val (V) | Ala, Ile, Leu, Met, Thr |

TABLE 1B

| Amino Acid Property | Amino Acid Substitutions |
| --- | --- |
| Hydrophobic | Cys, Ile, Leu, Met, Phe, Pro, Trp, Val |
| Aliphatic | Ala, Ile, Leu, Pro, Val |
| Aromatic | His, Phe, Trp, Tyr |
| Amide | Asn, Gln |
| Nucleophilic | Cys, Ser, Thr |
| Polar | Arg, Asp, Asn, Gln, Glu, Lys |
| Negative | Asp, Glu |
| Positive | Arg, Lys, His |
| Small | Ala, Gly, Pro, Ser |
| C-beta | Ile, Thr, Val |

As defined herein, the term "N-methylation" refers to a form of alkylation wherein a methyl group, $CH_3$, replaces the hydrogen atom of the NH moiety in the backbone amide NHs of the peptide analogue.

β-Substitution

For each amino acid, a β-amino acid or β-peptide refers to an ammo acid in which the amino group of $-NH_2$ is attached to the secondary carbon rather than the α carbon. For example, a methylene group ($CH_2$) is inserted into the side chain at the beta position of that side chain. The flexibility to generate a vast range of stereo- and regioisomers, together with the possibility of disubstitution, significantly expands the structural diversity of β-amino acids. For instance, the incorporation of β-amino acids has been successful in creating peptidomimetics that not only have potent biological activity, but are also resistant to proteolysis.

N-Terminal Modification

As used herein, the N-terminal modification refers to the modification of the $NH_2$ at the N-terminus, resulting in an R1 being linked to the NH moiety. N-terminal modifications are known to one of ordinary skill in the art. In some embodiments, N-terminal modification may comprise acylation. For example, an acylation modification comprising acetylation of the N-terminal results in R1 being an acetyl, —$COCH_3$, such that the N-terminus is $CH_3CO$—HN—. In other embodiments, R1 may comprise a —CO-A, wherein A is an optionally substituted alkyl group. For instance, R1 may comprise —CO—$(CH_2)_n CH_3$ or —CO—$(CH_2)CF_3$, where "n" can range from 0 to 10. When n=0, the R1 of the N-terminal is an acetyl. Without wishing to limit the invention to a particular theory or mechanism, N-terminal modifications may play a role in stability, protein folding, cellular attachment, and function modulation of the peptide analogue.

C-Terminal Modification

As used herein, C-terminal modification refers to the modification of the carboxyl moiety at the C-terminus. C-terminal modifications are known to one of ordinary skill in the art. As used herein, R2 refers to the standard —COOH of the C-terminal. Examples of C-terminal modifications include, but are not limited to, amidation, esterification, or reduction. In some embodiments, the C-terminal may be modified to be —$CONHR_3$, —COO-A, or —$CH_2OH$, where $R_3$ may be an H, $NH_2$, OH or an optionally substituted alkyl, and where A is selected from an optionally substituted alkyl group. For example, the C-terminal can be an amidated (e.g. —$CONH_2$. Without wishing to limit the invention to a particular theory or mechanism, C-terminal modifications, such as amidation, can enhance the biological activity of the peptide analogue, increase its stability, efficacy, and ability to enter cells, as well as increase its ability to resist enzymatic degradation.

Glycosylation

As used herein, the term "glycosylated" is defined as a saccharide (or sugar) covalently attached, i.e. linked, to an amino acid, resulting in a glycan, Specifically, the saccharide is linked to the side-chain of the amino acid. In some embodiments, the peptide analogue may be modified via glycosylation or with a glycan, at the N-terminal or C-terminal. Glycosylation processes and glycans are well known to one of ordinary skill in the art. In one aspect, the glycosylated amino acid may comprise a saccharide O-linked, N-linked, C-linked, or S-linked to a natural amino acid.

In some embodiments, the saccharide is attached to the hydroxyl group of the side-chain of the amino acid, such as Ser. Thr. or Tyr. In another aspect, the glycosylated amino acid may comprise a saccharide N-linked to a natural amino. For example, the saccharide is attached to the amine group of the side-chain of the amino acid, such as Asn or Lys. In other embodiments, glycosylation of the C-terminal may take place via an esterification reaction. Examples of saccharides include, but are not limited to, glucose, fructose, and lactose. In another aspect, the glycan may be selected from mono-, di-, tri- and poly-saccharides. In some embodiments, the glycosylated peptide analogue has an increased ability to cross a blood brain barrier (BBB) as compared to a peptide lacking the glycosylation.

Isosteres

As known to one of ordinary skill in the art, replacing of the peptide bond, i.e, the CONH, results in a peptide isostere. Without wishing to limit the invention to a particular theory or mechanism, the application of peptide isosteres with the objective to increase the metabolic stability of oligopeptides and to reduce their conformational flexibility can provide for peptide based bioactive molecules. Peptide isosteres are not composed of alpha amino acids but have structures and properties resembling those of "common" peptides. For example, dipeptide isosteres are designed to replace two amino acids and are functionalized with an amine and a carboxylate functionality. Non-limiting example of groups that can replace the peptide bond include, but are not limited to ester, N-alkylation, alkene, alyneamide to double bond, thioamide, amideoxy, azapeptide, and dehydroaminoacid.

Cyclization

The peptide analogues of the present invention may be cyclized thorough bridging of the residues via ring closing reactions. In particular, the side chain of a residue is linked to the side chain of another residue via a linker. In some embodiments, the linker $L_1$ is a carbo, lactam, disulfide, thioether, or succinic linker. As understood by one of ordinary skill in the art, the linker is not limited to the aforementioned examples, and may depend upon the specific cyclization chemistry used to produce the cyclic peptide. As a non-limiting example, residues can be linked via an amide bond formation reaction, which may form a —$(CH_2)$—CO—NH—$(CH_2)_n$-bridge, where n=1, 2, 3, 4. In addition, carbon-carbon bonds, lactone, thioether, ether, disulfide and other covalent bonds can be used as a part of the ring closing reactions. Without wishing to limit the invention to a particular theory or mechanism, the type of linker can affect the structural, chemical, and biological activity of the peptide ligand.

Blood-Brain Barrier: The blood-brain barrier is made up of brain microvessel endothelial cells characterized by tight intercellular junctions, minimal pinocytic activity, and the absence of fenestra. These characteristics endow these cells with the ability to restrict passage of most small polar blood-borne molecules (e.g., neurotransmitter catecholamines, small peptides) and macromolecules (e.g., proteins) from the cerebrovascular circulation to the brain. The blood-brain barrier contains highly active enzyme systems as well, which further enhance the already very effective protective function. It is recognized that transport of molecules to the brain is not determined solely by molecular size but by the permeabilities governed by specific chemical characteristics of the permeating substance. Thus, besides molecular size and lipophilicity, the affinity of the substances to various blood proteins, specific enzymes in the blood, or the blood-brain barrier may influence the amount of the drug and/or peptide analogue reaching the brain.

As used herein, the terms "treat", "treating", or "treatment" refer to both therapeutic treatment and prophylactic or preventative measures, with the objective of preventing, reducing, slowing down (lessen), inhibiting, or eliminating an undesired physiological change, symptom, or disorder, such as the development or spread of β-amyloid toxicity, for example, β-amyloid deposits and Alzheimer's disease. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with the peptide analogue of the invention may include reduction of undesirable β-amyloid toxicity, such as oxidative stress, synaptic dysfunction, and apoptosis or cell death. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the subject or patient may be identified (e.g., diagnosed) as one suffering from the disease or condition (e.g., Alzheimer's disease) prior to administration of the peptide analogue of the invention.

A "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disease being treated and the severity of the disease; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects.

The terms "administering" and "administration" refer to methods of providing a pharmaceutical composition to a subject. Such methods are well known to those skilled in the art and include, but are not limited to, administering the compositions orally, parenterally (e.g., intravenously and subcutaneously), by intramuscular injection, by intraperitoneal injection, intrathecally, transdermally, extracorporeally, topically or the like.

As described above, the compositions can be administered to a subject in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Typically, an appropriate amount of a pharmaceutically-acceptable salt is used in the formulation to render the formulation isotonic. Examples of the pharmaceutically-acceptable carrier include, but are not limited to, saline. Ringer's solution and dextrose solution. The pH of the solution may be about 5 to about 8, such as from about 7 to about 7.5. Further carriers include sustained release preparations such as semi-permeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more desirable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

For example, preparations for parenteral administration include sterile aqueous or non-aqueous solutions, suspensions, and emulsions. Examples of non-aqueous solvents are propylene glycol, polyethylene glycol, vegetable oils such as olive oil, fish oils, and injectable organic-esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils, intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration include but are not limited to, ointments, lotions, creams, gels, drops, suppositories, sprays, liquids and powders. Conventional pharmaceutical carriers, aqueous, powder or oily bases, thickeners and the like may be necessary or desirable. Pharmaceutical formulations for oral administration include, but are not limited to, powders or granules, suspensions or solutions in water or non-aqueous media, capsules, sachets, or tablets. Thickeners, flavorings, diluents, emulsifiers, dispersing aids or binders may be desirable.

Nerve cells, of which there are nearly 100 billion in the human brain, communicate by special contacts called 'synapses' (FIG. 1A). Complex communication in the brain occurs via approximately 100 trillion synapses. Each synapse is highly dynamic and can be regulated positively or negatively, short- and long-term potentiation, and long-term depression. Prior to AD, Aβ is released from nerve endings at synapses in response to nerve activity, Aβ in pM-nM concentrations has agonist-like activity at presynaptic nicotinic receptors (nAChRs) and can increase $Ca^{2+}$ in isolated synaptic terminals via nAChRs. In pM concentrations, Aβ augments long-term potentiation, Therefore, Pβ is active as a neuromodulator.

Figure 1B:
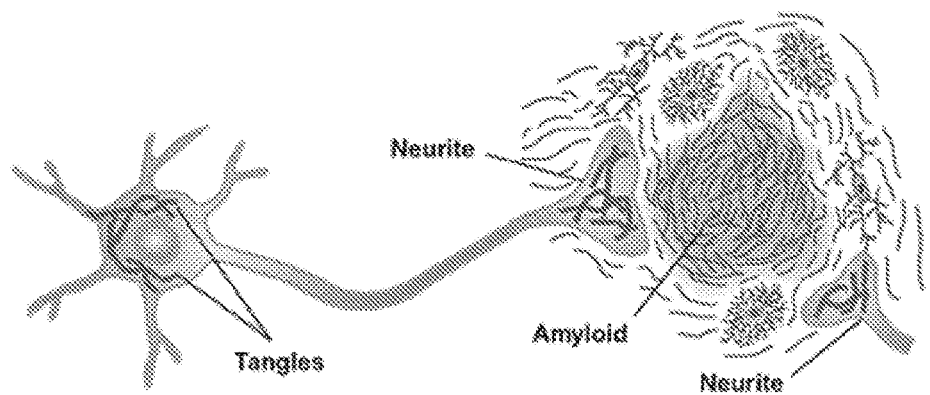
FIG. 1B shows a model of how plaques and tangles affect the synapse (Wong et al, Nature Neurosci, 5, 633-639, 2002).
Figure 1C:
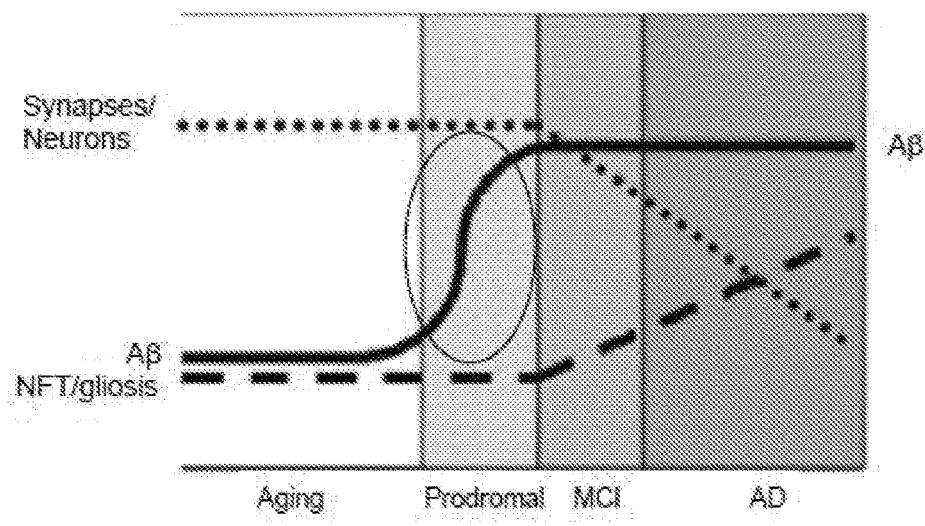
FIG. 1C shows a model of progression of AD pathology (Ingelsson et al., Neural. 62, 925-932, 2004).

In FIG. 1B, the plaques, which are composed of a sticky peptide called beta amyloid (Aβ), accumulate in the brain in AD, primarily near synapses. Abnormal tau, manifested as neurofibrillary tangles, is linked to neurotoxicity leading to neurodegeneration. In AD, the most notable early change is the dramatic loss of synapses. Referring to FIG. 1C, most beta amyloid is soluble and diffusible, therefore "floating" around the brain. Its levels rise sharply 5-15 years before the diagnosis of AD. After this rise, synapses and nerve cells start to die off.

Figure 2:
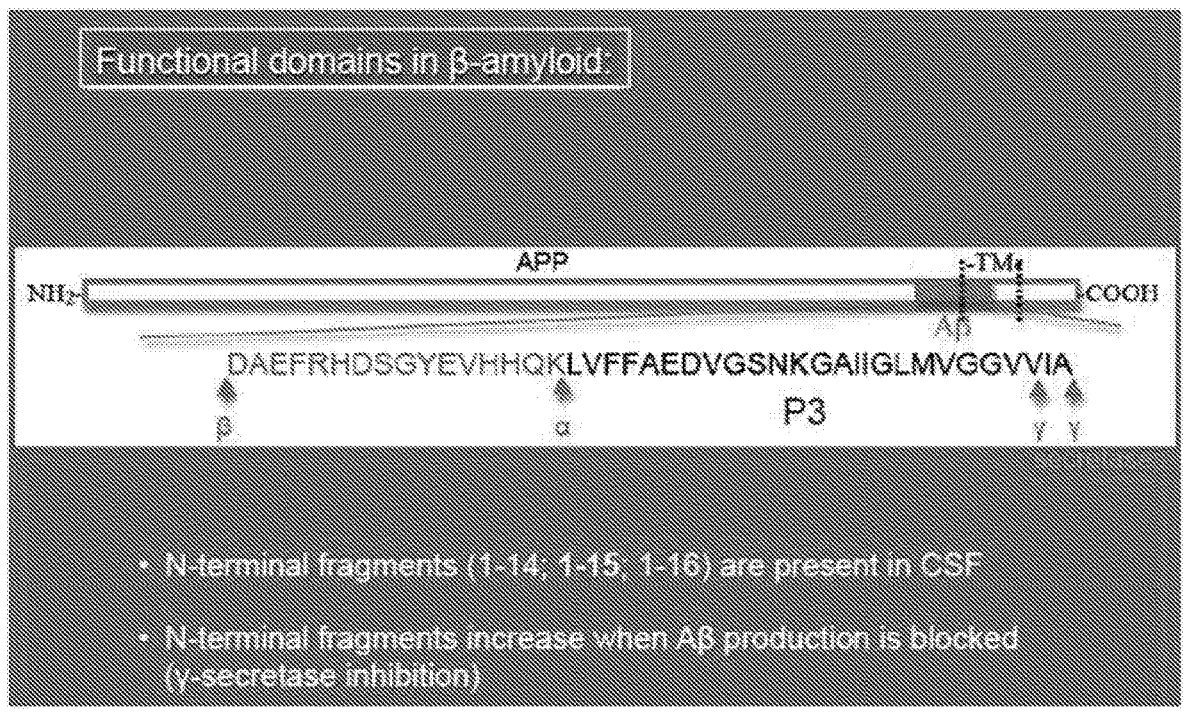
FIG. 2 shows the functional domains in β-amyloid. β-amyloid is cleaved from the amyloid precursor protein (APP) by the action of the β- and γ-secretases, and encompasses part of the APP transmembrane domain (TM). The N-terminal fragment (from the left, is produced from β-amyloid by the action of α-secretese.

As discussed, FIG. 2 shows that β-amyloid is cleaved from the amyloid precursor protein (APP). N-terminal Aβ fragments (1-14; 1-15; 1-16) are generated by the combined action of "α and β-secretases, and resident carboxypeptidase. The N-terminal Aβ fragment is present in the brains and CSF of healthy adults as well as in Alzheimer's patients. Unlike full-length oligomeric β-amyloid, the N-terminal Aβ fragment is monomeric and nontoxic. In $Ca^{2+}$ imaging studies, the N-terminal Aβ fragment has proven to be highly potent and more effective than full-length β-amyloid in its agonist-like action on nicotinic receptors. N-terminal Aβ fragments increase when Aβ production is blocked under conditions of reduced γ-secretase activity.

Figure 3:
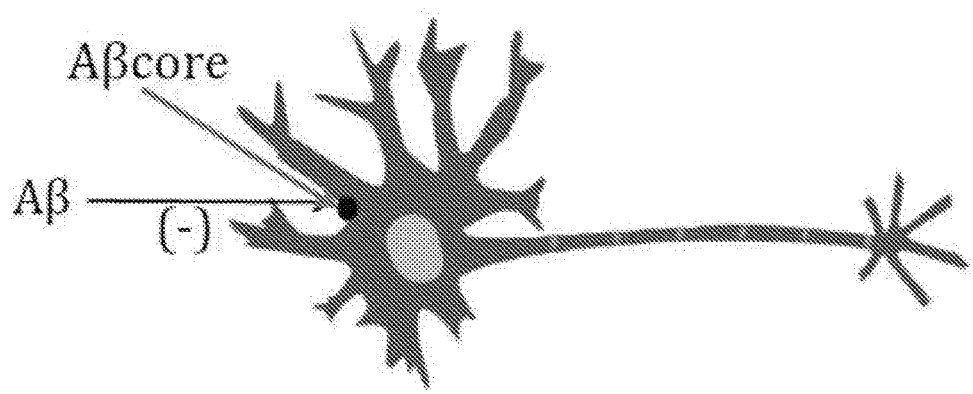
FIG. 3 shows the β-amyloid core fragment and β-amyloid in a competitive mechanism (direct or via differential receptor-based signaling).

Referring to FIG. 3, although high levels of β-amyloid interferes with synaptic dynamics and kills neurons, the addition of the non-toxic N-terminal Aβ fragments can prevent synaptic inhibition and cell death. Without wishing to limit the present invention to particular theory or mechanism, these N-terminal Aβ fragments are believed to participate in a direct or indirect competitive mechanism against the β-amyloid and/or Aβ-linked intracellular signaling pathways, hence, these N-fragments are neuroprotective. The present invention features peptide derivatives and peptidomimetics based on the neuroprotective core sequence fragment for use in treating Alzheimer's disease.

According to one embodiment, the present invention features a modified β-amyloid peptide analogue comprising a sequence at least 50% identical to YEVHHQ (SEQ ID NO. 1), in preferred embodiments, the HH is preserved. In some embodiments, any one of the residues may be conservatively substituted. In one embodiment, one, two, or three residues may be conservatively substituted, in another embodiment, the modified β-amyloid peptide analogue comprises a sequence that is at least 60% identical to SEQ ID NO. 1. For example, one or two residues may be conservatively substituted. In yet another embodiment, the modified β-amyloid peptide analogue comprises a sequence that is at least 80% identical to SEQ ID NO. 1. For example, at most one residue may be conservatively substituted. For example, the Q may be conservatively substituted with H. In further embodiments, the Y residue is preserved. In most instances, it may be desirable that any of the peptide analogues of the present invention be non-toxic and neuroprotective. Non-limiting examples of analogues based on SEQ ID NO. 1 are provided in Table 2.

TABLE 2

Sequences of modified β-amyloid peptide analogues based on SEQ ID NO. 1.

| SEQ ID NO | 1 | 2 | 3 | 4 | 5 | 6 | | Feature |
|---|---|---|---|---|---|---|---|---|
| 4 | R1 | Xaa | E | V | H*/#/° | H*/#/° | Q | R2 | Xaa is F, Y, or W |
| 5 | R1 | Y | Xaa | V | H*/#/° | H*/#/° | Q | R2 | Xaa is D or E |
| 6 | R1 | Y | E | Xaa | H*/#/° | H*/#/° | Q | R2 | Xaa is V, L, I, or M |
| 7 | R1 | Y | E | V | H*/#/° | H*/#/° | Xaa | R2 | Xaa is H, N or Q |
| 8 | R1 | Xaa | Yaa | V | H*/#/° | H*/#/° | Q | R2 | Xaa is F, Y, or W; Yaa is D or E |
| 9 | R1 | Xaa | E | Yaa | H*/#/° | H*/#/° | Q | R2 | Xaa is F, Y, or W; Yaa is V, L, I, or M; |
| 10 | R1 | Xaa | E | V | H*/#/° | H*/#/° | Yaa | R2 | Xaa is F, Y, or W; Yaa is H, N or Q |
| 11 | R1 | Y | Xaa | Yaa | H*/#/° | H*/#/° | Q | R2 | Xaa is D or E; Yaa is V, L, I, or M; |
| 12 | R1 | Y | Xaa | V | H*/#/° | H*/#/° | Yaa | R2 | Xaa is D or E; Yaa is H, N or Q |
| 13 | R1 | Y | E | Xaa | H*/#/° | H*/#/° | Yaa | R2 | Xaa is V, L, I, or M; Yaa is H, N or Q |
| 14 | R1 | Xaa | Yaa | Zaa | H*/#/° | H*/#/° | Q | R2 | Xaa is F, Y, or W; Yaa is D or E; Zaa is V, L, I, or M; |
| 15 | R1 | Xaa | Yaa | V | H*/#/° | H*/#/° | Zaa | R2 | Xaa is F, Y, or W; Yaa is D or E; Zaa is H, N or Q |
| 16 | R1 | Xaa | E | Yaa | H*/#/° | H*/#/° | Zaa | R2 | Xaa is F, Y, or W; Yaa is V, L, I, or M; Zaa is H, N or Q |
| 17 | R1 | Y | Xaa | Yaa | H*/#/° | H*/#/° | Zaa | R2 | Xaa is D or E; Yaa is V, L, I, or M; Zaa is H, N or Q |

*D-amino Acid,
°N-methylated,
Beta-substituted amino acid.
*/#/°refers to the residue being a D-amino Acid and/or N-methylated and/or a Beta-substituted amino acid.
R1 can be an acetyl, glycosylation, or —CO—$(CH_2)_n CH_3$ from N-terminal modifications.
R2 can be amidation, reduction or glycosylation from C-terminal modifications. In some embodiments, n can range from 1 to 10. It is understood that other permutations are possible and within the scope of the invention.

According to yet another embodiment, the present invention features a modified β-amyloid peptide analogue comprising a sequence at least 50% identical to DAEFRHO-SGYEVHHQ (SEQ ID NO. 2), with the caveat that HH is preserved. For example, at least 8 residues, including HH, of SEQ ID NO. 2 are preserved. According to another embodiment, the modified β-amyloid peptide analogue may comprise a sequence that is at least 60% identical to SEQ ID NO. 2. For example, at least 9 residues, including HH, of SEQ IQ NO. 2 are preserved. According to yet another embodiment, the modified β-amyloid peptide analogue may compose a sequence that is at least 70% identical to SEQ ID NO. 2. For example, at least 11 residues, including HH, of SEQ ID NO. 2 are preserved. According to a further embodiment, the modified β-amyloid peptide analogue may comprise a sequence that is at least 80% identical to SEQ ID NO. 2. For example, at least 12 residues, including HH, of SEQ ID NO. 2 are preserved. In an exemplary embodiment, the Y residue is preserved. In another exemplary embodiment, Q may be conservatively substituted with H. In most instances, it may be desirable that any of the peptide analogues of the present invention is non-toxic and neuroprotective.

In some embodiments, at most 7 residues of the $1^{st}$-$12^{th}$ and $15^{th}$ residues in SEQ ID NO. 2 may be conservatively substituted. In other embodiments, at most 6 residues of the $1^{st}$-$12^{th}$ and $15^{th}$ residues in SEQ ID NO. 2 may be conservatively substituted. In still other embodiments, at most 5 residues of the $1^{st}$-$12^{th}$ and $15^{th}$ residues in SEQ ID NO. 2 may be conservatively substituted. In one embodiment, at most 4 residues of the $1^{st}$-$12^{th}$ and $15^{th}$ residues in SEQ ID NO. 2 may be conservatively substituted. In another embodiment, at most 3 residues of the $1^{st}$-$12^{st}$ and $15^{th}$ residues in SEQ ID NO. 2 may be conservatively substituted. In yet another embodiment, at most 2 residues of the $1^{st}$-$12^{th}$ and $15^{th}$ residues in SEQ ID NO. 2 may be conservatively substituted. In a further embodiment, only 1 residue of the $1^{st}$-$12^{th}$ and $15^{th}$ residues in SEQ ID NO. 2 may be conservatively substituted. Non-limiting examples of said analogues based on SEQ ID NO. 2 are provided in Table 3.

TABLE 3

Sequences of modified β-amyloid peptide analogues based on SEQ ID NO. 2.

| SEQ ID NO | | 1-9 | 10 | 11 | 12 | 13 | 14 | 15 | | Feature |
|---|---|---|---|---|---|---|---|---|---|---|
| 18 | R1 | DAEFR*/#/°HDSG | Xaa | E | V | H*/#/° | H*/#/° | Q | R2 | Xaa is F, Y, or W |
| 19 | R1 | DAEFR*/#/°HDSG | Y | Xaa | V | H*/#/° | H*/#/° | Q | R2 | Xaa is D or E |
| 20 | R1 | DAEFR*/#/°HDSG | Y | E | Xaa | H*/#/° | H*/#/° | Q | R2 | Xaa is V, L, I, or M; |
| 21 | R1 | DAEFR*/#/°HDSG | Y | E | V | H*/#/° | H*/#/° | Xaa | R2 | Xaa is H, N or Q |
| 22 | R1 | DAEFR*/#/°HDSG | Xaa | Yaa | V | H*/#/° | H*/#/° | Q | R2 | Xaa is F, Y, or W; Yaa is D or E |
| 23 | R1 | DAEFR*/#/°HDSG | Xaa | E | Yaa | H*/#/° | H*/#/° | Q | R2 | Xaa is F, Y, or W; Yaa is V, L, I, or M; |
| 24 | R1 | DAEFR*/#/°HDSG | Xaa | E | V | H*/#/° | H*/#/° | Yaa | R2 | Xaa is F, Y, or W; Yaa is H, N or Q |
| 25 | R1 | DAEFR*/#/°HDSG | Y | Xaa | Yaa | H*/#/° | H*/#/° | Q | R2 | Xaa is D or E; Yaa is V, L, I, or M; |
| 26 | R1 | DAEFR*/#/°HDSG | Y | Xaa | V | H*/#/° | H*/#/° | Yaa | R2 | Xaa is D or E; Yaa is H, N or Q |
| 27 | R1 | DAEFR*/#/°HDSG | Y | E | Xaa | H*/#/° | H*/#/° | Yaa | R2 | Xaa is V, L, I, or M; Yaa is H, N or Q |
| 28 | R1 | DAEFR*/#/°HDSG | Xaa | Yaa | Zaa | H*/#/° | H*/#/° | Q | R2 | Xaa is F, Y, or W; Yaa is D or E; Zaa is V, L, I, or M; |
| 29 | R1 | DAEFR*/#/°HDSG | Xaa | Yaa | V | H*/#/° | H*/#/° | Zaa | R2 | Xaa is F, Y, or W; Yaa is D or E; Zaa is H, N or Q |
| 30 | R1 | DAEFR*/#/°HDSG | Xaa | E | Yaa | H*/#/° | H*/#/° | Zaa | R2 | Xaa is F, Y, or W; Yaa is V, L, I, or M; Zaa is H, N or Q |
| 31 | R1 | DAEFR*/#/°HDSG | Y | Xaa | Yaa | H*/#/° | H*/#/° | Zaa | R2 | Xaa is D or E; Yaa is V, L, I, or M; Zaa is H, N or Q |
| 32 | R1 | DAEF*/#/°-Waa-HDSG | Xaa | Yaa | Zaa | H*/#/° | H*/#/° | Q | R2 | Waa is H, K, or R; Xaa is F, Y, or W; Yaa is D or E; Zaa is V, L, I, or M; |
| 33 | R1 | DAEF*/#/°-Waa-HDSG | Xaa | Yaa | V | H*/#/° | H*/#/° | Zaa | R2 | Waa is H, K, or R; Xaa is F, Y, or W; Yaa is D or E; Zaa is H, N or Q |
| 34 | R1 | DAEF*/#/°-Waa-HDSG | Xaa | E | Yaa | H*/#/° | H*/#/° | Zaa | R2 | Waa is H, K, or R; Xaa is F, Y, or W; Yaa is V, L, I, or M; Zaa is H, N or Q |
| 35 | R1 | DAEF*/#/°-Waa-HDSG | Y | Xaa | Yaa | H*/#/° | H*/#/° | Zaa | R2 | Waa is H, K, or R; Xaa is D or E; Yaa is V, L, I, or M; Zaa is H, N or Q |
| 36 | R1 | DA-Vaa-F*/#/°-Waa-HDSG | Xaa | Yaa | Zaa | H*/#/° | H*/#/° | Q | R2 | Vaa is D or E; Waa is H, K, or R; Xaa is F, Y, or W; Yaa is D or E; Zaa is V, L, I, or M; |

TABLE 3-continued

Sequences of modified β-amyloid peptide analogues based on SEQ ID NO. 2.

| SEQ ID NO | 1-9 | | 10 | 11 | 12 | 13 | 14 | 15 | | Feature |
|---|---|---|---|---|---|---|---|---|---|---|
| 37 | R1 | DA-Vaa-F*/#/°-Waa-HDSG | Xaa | Yaa | V | H*/#/° | H*/#/° | Zaa | R2 | Vaa is D or E; Waa is H, K, or R; Xaa is F, Y, or W; Yaa is D or E; Zaa is H, N or Q |
| 38 | R1 | DA-Vaa-F*/#/°-Waa-HDSG | Xaa | E | Yaa | H*/#/° | H*/#/° | Zaa | R2 | Vaa is D or E; Waa is H, K, or R; Xaa is F, Y, or W; Yaa is V, L, I, or M; Zaa is H, N or Q |
| 39 | R1 | DA-Vaa-F*/#/°-Waa-HDSG | Y | Xaa | Yaa | H*/#/° | H*/#/° | Zaa | R2 | Vaa is D or E; Waa is H, K, or R; Waa is H, K, or R; Xaa is D or E; Yaa is V, L, I, or M; Zaa is H, N or Q |
| 40 | R1 | D-Uaa-Vaa-F*/#/°-Waa-HDSG | Xaa | Yaa | Zaa | H*/#/° | H*/#/° | Q | R2 | Uaa is A, G, or S; Vaa is D or E; Waa is H, K, or R; Xaa is F, Y, or W; Yaa is D or E; Zaa is V, L, I, or M |
| 41 | R1 | D-Uaa-Vaa-F*/#/°-Waa-HDSG | Xaa | Yaa | V | H*/#/° | H*/#/° | Zaa | R2 | Uaa is A, G, or S; Vaa is D or E; Waa is H, K, or R; Xaa is F, Y, or W; Yaa is D or E; Zaa is H, N or Q |
| 42 | R1 | D-Uaa-Vaa-F*/#/°-Waa-HDSG | Xaa | E | Yaa | H*/#/° | H*/#/° | Zaa | R2 | Uaa is A, G, or S; Vaa is D or E; Waa is H, K, or R; Xaa is F, Y, or W; Yaa is V, L, I, or M; Zaa is H, N or Q |
| 43 | R1 | D-Uaa-Vaa-F*/#/°-Waa-HDSG | Y | Xaa | Yaa | H*/#/° | H*/#/° | Zaa | R2 | Uaa is A, G, or S; Vaa is D or E; Waa is H, K, or R; Xaa is D or E; Yaa is V, L, I, or M; Zaa is H, N or Q |
| 44 | R1 | Taa-Uaa-Vaa-F*/#/°-Waa-HDSG | Xaa | Yaa | Zaa | H*/#/° | H*/#/° | Q | R2 | Taa is D or E; Uaa is A, G, or S; Vaa is D or E; Waa is H, K, or R; Xaa is F, Y, or W; Yaa is D or E; Zaa is V, L, I, or M |
| 45 | R1 | Taa-Uaa-Vaa-F*/#/°-Waa-HDSG | Xaa | Yaa | V | H*/#/° | H*/#/° | Zaa | R2 | Taa is D or E; Uaa is A, G, or S; Vaa is D or E; Waa is H, K, or R; Xaa is F, Y, or W; Yaa is D or E; Zaa is H, N or Q |
| 46 | R1 | Taa-Uaa-Vaa-F*/#/°-Waa-HDSG | Xaa | E | Yaa | H*/#/° | H*/#/° | Zaa | R2 | Taa is D or E; Uaa is A, G, or S; Vaa is D or E; Waa is H, K, or R; Xaa is F, Y, or W; Yaa is V, L, I, or M; Zaa is H, N or Q |
| 47 | R1 | Taa-Uaa-Vaa-F*/#/°-Waa-HDSG | Y | Xaa | Yaa | H*/#/° | H*/#/° | Zaa | R2 | Taa is D or E; Uaa is A, G, or S; Vaa is D or E; Waa is H, K, or R; Xaa is D or E; Yaa is V, L, I, or M; Zaa is H, N or Q |

*D-amino Acid,
°N-methylated,
Beta-substituted amino acid.
*/#/° refers to the residue being a D-amino Acid and/or N-methylated and/or a Beta-substituted amino acid.
R1 can be an acetyl, glycosylation, or —CO—(CH$_2$)$_n$CH$_3$ from N-terminal modifications.
R2 can be amidation, reduction or glycosylation from C-terminal modifications. In some embodiments, n can range from 1 to 10. It is understood that other permutations are possible and within the scope of the invention.

According to another embodiment, the present invention features a modified β-amyloid peptide analogue being at least 50% identical to at least a YEVHHQ fragment of DAEFRHDSGYEVHHQ (SEQ ID NO. 2), with the caveat that HH is preserved. In one embodiments, the peptide analogue may comprise a sequence according to the following:

$$X_1X_2\ X_3X_4\ X_5X_6\ X_7X_8\ X_9X_{10}\ X_{11}X_{12}HHX_{15} \quad \text{(SEQ ID NO. 3)}$$

In another embodiment, the peptide analogue may be at least 60% identical to YEVHHQ of SEQ ID NO. 2. In yet another embodiment the peptide analogue is at least 80% identical to YEVHHQ of SEQ ID NO. 2. In some embodiments, any of the $X_1$-$X_9$ residues may be optionally present in the peptide analogue. In other embodiments, one or more residues from $X_1$-$X_9$ may be absent (i.e., no amino acid may be in those positions). In one embodiment, the first amino acid of the peptide analogue may be at position $X_2$, $X_3$, $X_4$, $X_5$, $X_6$, $X_7$, $X_8$, $X_9$, or $X_{10}$. In other embodiments, the $X_{18}$ residue may be optionally present, i.e., the $X_{15}$ residue may be absent. For example, the last amino acid may be the terminal His.

In some embodiments, the peptide analogue is at least 5 amino acids in length. In other embodiments, the peptide analogue is at least 6 amino acids in length. In yet other embodiments, the peptide analogue is at least 7 amino acids in length. In still other embodiments, the peptide analogue is at least 8 amino acids in length. In further embodiments the peptide analogue is at least 9 amino acids in length. In some embodiments, the peptide analogue is at least 10 amino acids in length. In other embodiments, the peptide analogue is at least 11 amino acids in length. In yet other embodiments, the peptide analogue is at least 12 amino acids in length. In still other embodiments, the peptide analogue is at least 13 amino acids in length. In further embodiments, the peptide analogue is at least 14 amino acids in length. In still further embodiments, the peptide analogue is at least 15 amino acids in length.

In one embodiment, $X_1$ may be Asp, or a conservative substitution thereof (e.g. Asn, Gln, Glu, Ser). Conservative substitutions tor each natural amino acid are listed in TABLE 1A and 1B. In another embodiment, $X_2$ may be Ala, or a conservative substitution thereof. In yet another embodiment, $X_3$ may be Glu, or a conservative substitution thereof. In a further embodiment, $X_4$ may be Phe, or a conservative substitution thereof. In yet a further embodiment, $X_5$ may be Arg, or a conservative substitution thereof. In one embodiment, $X_6$ may be His, or a conservative substitution thereof. In another embodiment, $X_7$ may be Asp, or a conservative substitution thereof. In yet another embodiment, $X_8$ may be Ser, or a conservative substitution thereof. In still another embodiment, $X_9$ may be Gly, or a conservative substitution thereof. In a further embodiment, the $X_{10}$ may be Tyr that is preserved. In an alternative embodiment, $X_{10}$ may be Tyr, or a conservative substitution thereof. In yet a further embodiment, $X_{11}$ may be Glu, or a conservative substitution thereof. In still a further embodiment, $X_{12}$ may be Val, or a conservative substitution thereof. In one embodiment, $X_{15}$ may be Gln, His or a conservative substitution thereof. In yet a further embodiment, $X_1$-$X_{12}$ and $X_{15}$ may each be independently selected from natural and unnatural amino acids.

According to yet another embodiment, the modified β-amyloid peptide analogue is derived from DAEFRHDSGYEVHHQ (SEQ ID NO. 2), with a caveat that NH is preserved. In one embodiment, the peptide analogue may comprise a sequence according to the following:

$$X_1X_2\ X_3X_4\ X_5X_6\ X_7X_8\ X_9X_{10}\ X_{11}X_{12}HHX_{15} \quad \text{(SEQ ID NO. 3)}$$

Consistent with previous embodiments, the $X_1$-$X_9$ residues may optionally be present in the peptide analogue. In other embodiments, the $X_1$-$X_{12}$ and $X_{15}$ residues may each be independently selected from natural and unnatural amino acids.

Non-limiting examples of said peptide analogues according to SEQ ID NO. 3 are provided in Table 4. It is understood that other permutations are possible and within the scope of the invention.

TABLE 4

Sequences of modified β-amyloid peptide analogues according to SEQ ID NO. 3.

| SEQ ID NO | $X_1$-$X_9$ | $X_{10}$ | $X_{11}$ | $X_{12}$ | $X_{13}$ | $X_{14}$ | $X_{15}$ | Feature |
|---|---|---|---|---|---|---|---|---|
| 48 | R1 DAEF*/#/°R-Taa-DSG | Xaa | E | V | H*/#/° | H*/#/° | Q | R2 Taa is H, K, or R; Xaa is F, Y, or W; |
| 49 | R1 DAEF*/#/°R-Taa-DSG | Xaa | Yaa | V | H*/#/° | H*/#/° | Q | R2 Taa is H, K, or R; Xaa is F, Y, or W; Yaa is D or E; |
| 50 | R1 DAEF*/#/°R-Taa-DSG | Xaa | E | Yaa | H*/#/° | H*/#/° | Zaa | R2 Taa is H, K, or R; Xaa is F, Y, or W; Yaa is V, L, I, or M; Zaa is H, N or Q |
| 51 | R1 DAEF*/#/°-R-TaaDSG | Y | Xaa | Yaa | H*/#/° | H*/#/° | Zaa | R2 Taa is H, K, or R; Xaa is D or E; Yaa is V, L, I, or M; Zaa is H, N or Q |
| 52 | R1 DAEFR*/#/°-Taa-Uaa-SG | Xaa | E | V | H*/#/° | H*/#/° | Q | R2 Taa is H, K, or R; Uaa is D or E; Xaa is F, Y, or W; |
| 53 | R1 DAEFR*/#/°-Taa-Uaa-SG | Xaa | Yaa | V | H*/#/° | H*/#/° | Q | R2 Taa is H, K, or R; Uaa is D or E; Xaa is F, Y, or W; Yaa is D or E; |

TABLE 4-continued

Sequences of modified β-amyloid peptide analogues according to SEQ ID NO. 3.

| SEQ ID NO | R1 | $X_1$-$X_9$ | $X_{10}$ | $X_{11}$ | $X_{12}$ | $X_{13}$ | $X_{14}$ | $X_{15}$ | R2 | Feature |
|---|---|---|---|---|---|---|---|---|---|---|
| 54 | R1 | DAEFR*/#/°-Taa-Uaa-SG | Xaa | E | Yaa | H*/#/° | H*/#/° | Zaa | R2 | Taa is H, K, or R; Uaa is D or E; Xaa is F, Y, or W; Yaa is V, L, I, or M; Zaa is H, N or Q |
| 55 | R1 | DAEFR*/#/°-Taa-Uaa-SG | Y | Xaa | Yaa | H*/#/° | H*/#/° | Zaa | R2 | Taa is H, K, or R; Uaa is D or E; Xaa is D or E; Yaa is V, L, I, or M; Zaa is H, N or Q |
| 56 | R1 | DAEFR-Taa*/#/°-Uaa-Vaa-G | Xaa | E | V | H*/#/° | H*/#/° | Q | R2 | Taa is H, K, or R; Uaa is D or E; Vaa is A, G, or S; Xaa is F, Y, or W |
| 57 | R1 | DAEFR-Taa*/#/°-Uaa-Vaa-G | Xaa | Yaa | V | H*/#/° | H*/#/° | Q | R2 | Taa is H, K, or R; Uaa is D or E; Vaa is A, G, or S; Xaa is F, Y, or W; Yaa is D or E |
| 58 | R1 | DAEFR-Taa*/#/°-Uaa-Vaa-G | Xaa | E | Yaa | H*/#/° | H*/#/° | Zaa | R2 | Taa is H, K, or R; Uaa is D or E; Vaa is A, G, or S; Xaa is F, Y, or W; Yaa is V, L, I, or M; Zaa is H, N or Q |
| 59 | R1 | DAEFR-Taa*/#/°-Uaa-Vaa-G | Y | Xaa | Yaa | H*/#/° | H*/#/° | Zaa | R2 | Taa is H, K, or R; Uaa is D or E; Vaa is A, G, or S; Xaa is D or E; Yaa is V, L, I, or M; Zaa is H, N or Q |
| 60 | R1 | AEFR-Taa-Uaa-Vaa-Waa | Xaa*/#/° | E | V | H*/#/° | H*/#/° | Q | R2 | Taa is H, K, or R; Uaa is D or E; Vaa is A, G, or S; Waa is A, G, or S; Xaa is F, Y, or W |
| 61 | R1 | EFR-Taa-Uaa-Vaa-Waa | Xaa*/#/° | Yaa | V | H*/#/° | H*/#/° | Q | R2 | Taa is H, K, or R; Uaa is D or E; Vaa is A, G, or S; Waa is A, G, or S; Xaa is F, Y, or W; Yaa is D or E |
| 62 | R1 | FR-Taa-Uaa-Vaa-Waa | Xaa*/#/° | E | Yaa | H*/#/° | H*/#/° | Zaa | R2 | Taa is H, K, or R; Uaa is D or E; Vaa is A, G, or S; Waa is A, G, or S; Xaa is F, Y, or W; Yaa is V, L, I, or M; Zaa is H, N or Q |
| 63 | R1 | R-Taa-Uaa-Vaa-Waa | Y*/#/° | Xaa | Yaa | H*/#/° | H*/#/° | Zaa | R2 | Taa is H, K, or R; Uaa is D or E; Vaa is A, G, or S; Waa is A, G, or S; Xaa is D or E; Yaa is V, L, I, or M; Zaa is H, N or Q |

*D-amino Acid,
°N-methylated,
Beta-substituted amino acid.
*/#/°refers to the residue being a D-amino Acid and/or N-methylated and/or a Beta-substituted amino acid.
R1 can be an acetyl, glycosylation, or —CO—(CH$_2$)$_n$CH$_3$ from N-terminal modifications.
R2 can be amidation, reduction or glycosylation from C-terminal modifications. In some embodiments, n can range from 1 to 10. In some embodiments, n can range from 1 to 10.

In preferred embodiments, it may be desirable that the peptide analogues of the present invention be non-toxic and neuroprotective. Without wishing to be bound to a particular theory or mechanism, the peptide analogues of the present invention are capable of competitive binding against β-amyloid for target sites or activation of pathways, such as alternative pathways (e.g. anti-apoptotic pathways and/or anti-oxidative pathways), thereby blocking or reversing the process by which the β-amyloid induces neurotoxicity.

In some embodiments, any of the modified β-amyloid peptide analogues described herein may comprise an N-terminal modification such as, for example, acetylation or glycosylation. In other embodiments, any of the modified β-amyloid peptide analogues may comprise a C-terminal modification such as, for example, amidation, esterification or glycosylation. In further embodiments, any of the modified β-amyloid peptide analogues may be cyclized.

In one embodiment, at least one of the residues in SEQ ID NO. 1, SEQ ID NO. 2, or SEQ ID NO. 3 may be n-methylated. In another embodiment, at least one of the residues in SEQ ID NO. 1, SEQ ID NO. 2, or SEQ ID NO. 3 may be a D-amino acid. In a further embodiment, at least one of the residues in SEQ ID NO, 1, SEQ ID NO. 2, or SEQ ID NO. 3 may be a β-substituted amino acid. In yet another embodiment, at least one of the residues in SEQ ID NO. 1, SEQ ID NO. 2, or SEQ ID NO. 3 can have multiple modifications. For example, the residue may be a D-amino acid that has been N-methylated. In other embodiments, at least one of the residues in SEQ ID NO. 1, SEQ ID NO. 2, or SEQ ID NO. 3 may be a peptide isostere.

According to another embodiment, the present invention features a method of treating Alzheimer's disease in a subject in need of such treatment. The method may comprise administering to the subject a therapeutically effective amount of a composition comprising any of the modified β-amyloid peptide analogues described herein, in a pharmaceutically acceptable carrier. Without wishing to limit the invention to a particular theory or mechanism, it is believed that the peptide analogues can be administered in a manner to effectively reduce or terminate synaptic inhibition and neuron death, thereby reducing the neurodegenerative effects of Alzheimer's disease.

According to a further embodiment, the present invention features a method of preventing Alzheimer's disease in a subject. The method may comprise administering to the subject a therapeutically effective amount of a composition comprising any of the modified β-amyloid peptide analogues described herein, in a pharmaceutically acceptable carrier. Without wishing to limit the invention to a particular theory or mechanism, it is believed that the peptide analogues can be administered in a manner to effectively prevent synaptic inhibition and neuron death, thereby preventing Alzheimer's disease in the subject.

According to some embodiments, the present invention features a method of treating or preventing a symptom associated with Alzheimer's Disease (AD) in a subject. In exemplary embodiments, the symptom may be associated with β-amyloid deposits, such as β-amyloid plaques. The method may comprise administering to the subject a therapeutically effective amount of a composition comprising any of the modified β-amyloid peptide analogues described herein, in a pharmaceutically acceptable carrier. Without wishing to be bound to a particular theory or mechanism, the peptide analogue may be administered in a manner to effectively terminate synaptic inhibition and neuron death.

According to other embodiments, the present invention features a method of treating or preventing a symptom associated with β-amyloid-induced toxicity in a subject. In exemplary embodiments, the β-amyloid-induced toxicity may be associated with oxidative stress and apoptosis. The method may comprise administering to the subject a therapeutically effective amount of a composition comprising any of the modified β-amyloid peptide analogues described herein, in a pharmaceutically acceptable carrier.

According to further embodiments, the present invention features a method of treating, reducing or inhibiting a disease or condition in a subject by administering to the subject a therapeutically effective amount of a composition comprising any of the modified β-amyloid peptide analogues described herein, in a pharmaceutically acceptable carrier. In exemplary embodiments, the disease or condition may be associated with synaptic inhibition or neuron death, such as, for example, Alzheimer's disease.

In some embodiments, the present invention features a composition for use in treating or preventing Alzheimer's disease. The composition may comprise any of the modified β-amyloid peptide analogues described herein, in a pharmaceutically acceptable carrier. In preferred embodiments, the composition is administered to a subject, where the composition comprises a therapeutically effective amount of the modified β-amyloid peptide.

In other embodiments, the present invention features a composition for use in treating or preventing a symptom associated with Alzheimer's Disease. The symptom may be associated with β-amyloid deposits, such as β-amyloid plaques. The composition may comprise any of the modified β-amyloid peptide analogues described herein, in a pharmaceutically acceptable carrier.

In yet other embodiments, the present invention features a composition for use in treating or preventing a symptom associated with β-amyloid-induced toxicity. For example, the β-amyloid-induced toxicity may be associated with oxidative stress and apoptosis. The composition may comprise any of the modified β-amyloid peptide analogues described herein, in a pharmaceutically acceptable carrier.

In further embodiments, the present invention features a composition for use in treating, reducing or inhibiting a disease or condition being associated with synaptic inhibition or neuron death. The composition may comprise any of the modified β-amyloid peptide analogues described herein in a pharmaceutically acceptable carrier. In one embodiment, the disease may be Alzheimer's disease.

In preferred embodiments, the composition comprising a therapeutically effective amount of the modified β-amyloid peptide is administered to a subject. Without wishing to limit the invention to a particular theory or mechanism, the compositions described herein may be effective for delivering the modified β-amyloid peptide analogue through the blood brain barrier. The modified β-amyloid peptide analogue may also be effective to reduce or terminate synaptic inhibition and neuron death. Further still, the modified β-amyloid peptide analogue can reduce a neurodegenerative effect of Alzheimer's disease.

According to some embodiments, the present invention features the use of a therapeutically effective amount of any of the modified β-amyloid peptide analogues described herein in preparation of a medicament for treatment or prevention of Alzheimer's disease in a subject. In one embodiment, the medicament may comprise the modified β-amyloid peptide is in a pharmaceutically-acceptable carrier. The medicament may be administered to the subject twice a day, daily, or every other day. Also, the medicament may be administered to the subject intranasally, intravenously, transdermally, or orally. In some embodiments, the medicament is effective for delivering the modified β-amyloid peptide analogue through the blood brain barrier. Without wishing to limit the invention to a particular theory or mechanism, the modified β-amyloid peptide analogue is effective to reduce or terminate synaptic inhibition and neuron death, or to reduce a neurodegenerative effect of Alzheimer's disease.

According to other embodiments, the present invention features the use of a therapeutically effective amount of any of the modified β-amyloid peptide analogues described herein in preparation of a medicament for treatment or prevention of a symptom associated with Alzheimer's Disease. In exemplary embodiments, the symptom may associated with β-amyloid deposits, such as β-amyloid plaques. Without wishing to be bound by a particular theory or mechanism, the modified β-amyloid peptide analogue may be effective to prevent, reduce or terminate synaptic inhibition and neuron death.

In still other embodiments, the present invention features the use of a therapeutically effective amount of any of the modified β-amyloid peptide analogues described herein in preparation of a medicament for for treatment or prevention of a symptom associated with β-amyloid-induced toxicity. Without wishing to be bound by a particular theory or mechanism, the modified β-amyloid peptide analogue may be effective to prevent, reduce or terminate the β-amyloid-induced toxicity associated with oxidative stress and apoptosis.

According to further embodiments, the present invention features the use of a therapeutically effective amount of any of the modified β-amyloid peptide analogues described herein in preparation of a medicament for treating, reducing or inhibiting a disease or condition being associated with synaptic inhibition or neuron death. In an exemplary embodiment, the disease may be Alzheimer's disease, Without wishing to be bound by a particular theory or mechanism, the modified β-amyloid peptide analogue may be effective to prevent, reduce or terminate synaptic inhibition and neuron death.

For any of the methods or uses of the composition described above, in some embodiments, the therapeutically effective amount of the modified β-amyloid peptide analogue is from about 0.001 mg/kg to 500 mg/kg of body weight, or any range in between, in some embodiments, the therapeutically effective amount is within the range of about 0.001 mg/kg to about 0.01 mg/kg, or within the range of about 0.01 mg/kg to about 0.1 mg/kg, or within the range of about 0.1 mg/kg to about 0.5 mg/kg, or within the range of about 0.5 mg/kg to about 1 mg/kg. In other embodiments, the therapeutically effective amount is within the range of about 1 mg/kg to about 2.5 mg/kg, or within the range of about 2.5 mg kg to about 10 mg/kg, or within the range of about 10 mg/kg to about 50 mg/kg. In still other embodiments, the therapeutically effective amount is within the range of about 50 mg/kg to about 100 mg/kg, or within the range of about 100 mg/kg to about 250 mg/kg, or within the range of about 250 mg/kg to about 500 mg/kg. In another embodiment, the therapeutically effective amount is an amount that is therapeutically effective in a mouse model. In further embodiments, the therapeutically effective amount of the modified β-amyloid peptide analogue may be administered twice a day, daily, or every other day. In still further embodiment, the therapeutically effective amount of the modified β-amyloid peptide analogue is administered intranasally, intravenously, transdermally, or orally.

The terms "dose" or "dosage" as used herein refers to a physically discrete unit of a formulation appropriate for a subject to be treated (e.g., for a single dose). Each dose contains a predetermined quantity of an active agent, e.g. the modified β-amyloid peptide analogue, selected to produce a desired therapeutic effect when administered according to a therapeutic regimen (it being understood that multiple doses may be required to achieve a desired or optimum effect). The dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be understood, however, that the total daily usage of a formulation of the present invention will be decided by the attending physician within the scope of sound medical judgment. The specific effective dose level for any particular subject or organism may depend upon a variety of factors including the severity of the disease; activity of the specific active peptides employed; specific composition employed; age, body weight, general health, sex and diet of the subject; time of administration, and rate of excretion of the specific active peptides employed; duration of the treatment; drugs and/or additional therapies used in combination or coincidental with specific compound(s) employed, and like factors well known in the medical arts.

In some embodiments, the modified β-amyloid peptide analogue is administered in a dosage of about 0.001 mg/kg to 500 mg/kg of body weight, or any range in between. For example, the dosage of the peptide analogue may be 0.001 mg/kg of body weight, or 0.01 mg/kg of body weight or 0.1 mg/kg of body weight. For example, a human weighing 55 kg may be administered about 0.055 mg of the peptide analogue per dose. In other embodiments, the composition is administered twice a day, daily, or every other day.

In one aspect, the modified β-amyloid peptide analogue composition can be administered in an intravenous dosage. This dosage can be administered to a subject once daily or in divided dosages throughout a day, as determined by methods known in the art. Its some embodiments of treatment, the dosage to a subject will require long term application to provide for a steady, long term stimulation of CNS tissue, which may require days, weeks, or months of treatment. It is contemplated that the dosage of the modified β-amyloid peptide analogue composition can be administered as infrequently as once every week or every two weeks, or at any interval in between, depending on a subject's clinical response to the medication. Moreover, if a subject does not respond to the initial dosage and administration of the modified β-amyloid peptide analogue composition, a person of skill can administer the medication daily for several days until such response occurs. A person of skill can monitor a subject's clinical response to the administration of the modified β-amyloid peptide analogue composition, and administer additional dosages as needed. It is contemplated that the modified β-amyloid peptide analogue composition can be administered to a subject on a daily basis, on an alternating daily basis, on a weekly basis, on a monthly basis, or at any interval in between.

In another aspect, the modified β-amyloid peptide analogue composition can be administered to a subject transdermally, by using an adherent patch, by using iontophoresis, or by using any other method known to a person of skill. The dosage of the modified β-amyloid peptide analogue composition, administered transdermally can be given daily or infrequently as once every 1 to 4 weeks. A person of skill, monitoring a subject's clinical response and improvement, can determine the frequency of administration of the medication by methods known in the art.

In certain embodiments, the modified β-amyloid peptide analogue composition can be administered to a subject by topical intranasal administration (intranasally) or administration by inhalant, in a dosage taken once daily or in divided doses. Further, the medication can be administered as infrequently as once every 1 to 4 weeks. A person of skill, monitoring a subject's clinical response to the administration of the medication, can adjust the frequency of administration according to methods known in the art. As used herein, "topical intranasal administration" means delivery of the compositions into the nose and nasal passages through one or both of the nares and can comprise delivery by a spraying mechanism (device) or droplet mechanism (device), or through aerosolization of the composition. Administration of the compositions by inhalant can be through the nose or mouth via delivery by a spraying or droplet mechanism. As used herein, "an inhaler" can be a spraying device or a droplet device for delivering the modified β-amyloid peptide analogue, in a pharmaceutically acceptable carrier, to the nasal passages and the upper and/or lower respiratory tracts of a subject. Delivery can also be directly to any area of the respiratory system (e.g., lungs) via intratracheal intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation.

In another aspect, the modified β-amyloid peptide analogue composition can be administered to a subject in a dosage taken once daily or in divided doses. Furthermore, the medication can be administered as infrequently as once every 1 to 4 weeks. A person monitoring a subject's clinical response can adjust the frequency of administration of the medication based on methods known in the art.

Transient reversible modification of the blood-brain barrier can be accomplished by osmotic opening, which is based on increasing capillary permeability by osmotically induced shrinkage of the endothelial cells which caused widening of the intercellular tight junctions. The osmotic load is generally a hyperosmotic water-soluble agent such as mannitol or arabinose. Briefly, under general anesthesia, a transfemoral catheter is introduced into the internal carotid or vertebral artery and 100-300 ml infusion of 25% mannitol is administered at 6-10 mg/sec for 30 seconds. An intravenous infusion of the pharmaceutical composition is begun approximately five to seven minutes before the mannitol infusion and is continued for 15 minutes. The transfemoral catheter is removed and the patient observed for 24-48 hours.

Alternatively, the modified β-amyloid peptide analogue may be linked to the osmotic agent (mannitol, arabinose, glucose or other sugar moiety), and a single infusion may be used. Conventional techniques may be used to link the modified β-amyloid peptide analogue and the osmotic agent. The linked agent itself will then cause the osmotically-induced shrinkage of the endothelial cells in order to widen the tight intercellular junctions. The linked agent may be designed such that the modified β-amyloid peptide analogue is cleaved from the linked agent after the BBB has been crossed.

EXPERIMENTAL

Current experiments relating to the invention have been preclinical using cell culture and animal models. Without wishing to limit the invention to a particular theory or mechanism, the core six-amino-acid beta amyloid peptide (N-Aβcore) has consistently prevented or reversed beta amyloid-induced neurotoxicity, inhibition of synaptic dynamics and spatial memory deficits.

In Vitro Neuronal Models. The studies were, performed on the NG108-15 rodent hybrid neuroblastoma cell line and primary hippocampal neuron cultures. The cell line can be differentiated, yielding axonal neurites with presynaptic-like varicosities that have the ability to release acetylcholine via exocytosis in response to stimulation. In addition, this model system does not endogenously express nicotinic receptors, allowing selective exogenous gene sequence expression of the target. The primary hippocampal neuron cultures provide a physiologically relevant model. Non-limiting examples of results are shown in FIGS. 4, 5A-5B, 8A-6B, 7A-7B, 8, 9A-9B, 10A-10B, 13A-13,C and 14A-14B.

Neuroblastoma Clonal Cell Culture and Transfection. Rodent hybrid neuroblastoma NG108-15 cells were used as a model nerve cell system allowing reconstitution with defined target receptors for Aβ. The cells were cultured in Dulbecco's modified Eagle's medium (DMEM) containing 15% fetal bovine serum (FBS) and differentiated in the presence of reduced serum (1% FBS) and 1 mM dibutyryl cyclic AMP for 72 h, Expression vectors (pcDNA3.1) containing mouse sequences for α4 and β2 nAChR subunits (1:4 ratio respectively) were transiently transfected into the cells using FuGENE HD (ThernioFisher, catalog #PRE2311) for 48 h. Mock-transfected NG108-15 cells, exposed only to FuGENE HO and not plasmid DNA, were used as controls.

Hippocampal Neuron Culture. All animal procedures followed an tACUC-approved protocol in accordance with animal welfare guidelines, Hippocampal neuron cultures even prepared from neonatal mouse pups (0-2d old) of either gender (roughly equivalent numbers) obtained from established colonies of wild-type B6.SJL (background) mice. Following rapid decapitation, brains were removed into ice-cold Neurobasal A medium (NB) containing B-27 supplement, 5% fetal bovine serum and Gentamicin (serum NB). Hippocampi were then isolated under a stereomicroscope. The hippocampi were digested with papain (Worthington, catalog #35N16202) in Hanks with 10 mM cysteine at 37° C. for 15 mins. The preparations were washed by centrifugation in serum NB. The cells were dissociated using sequential trituration with polished Pasteur pipettes of decreasing diameter and collected by low-speed centrifugation. The dissociated cells were preplated in standard tissue culture dishes to remove adherent non-neuronal cells (glia; fibroblasts) for 10-15 mins. The neuron-enriched supernatant was diluted to $1 \times 10^5$ cells/mL and plated into poly-D-lysine-coated 24-well dishes or onto Cell Tak-coated coverslips in serum NB. The cultures were maintained in Neurobasal A medium containing B27 and Gentamicin for 7-10 days prior to treatment.

$Ca^{2+}$ Imaging Fluo-4, a $Ca^{2+}$ indicator dye, was loaded into cells on coverslips and visualization of $[Ca^{2+}]$ was done via a Nikon PCM 2000 Cameleon AOTF confocal microscope. Each time-series was normalized to baseline fluorescence intensity at time zero (F/F0). After recording a baseline image series, each treatment was perfused over cells for 2.5 minutes or 15 minutes and quantification of relative fluorescence changes was analyzed through imageJ. Non-limiting examples of results are shown in FIG. 13A-13C.

Figure 11:
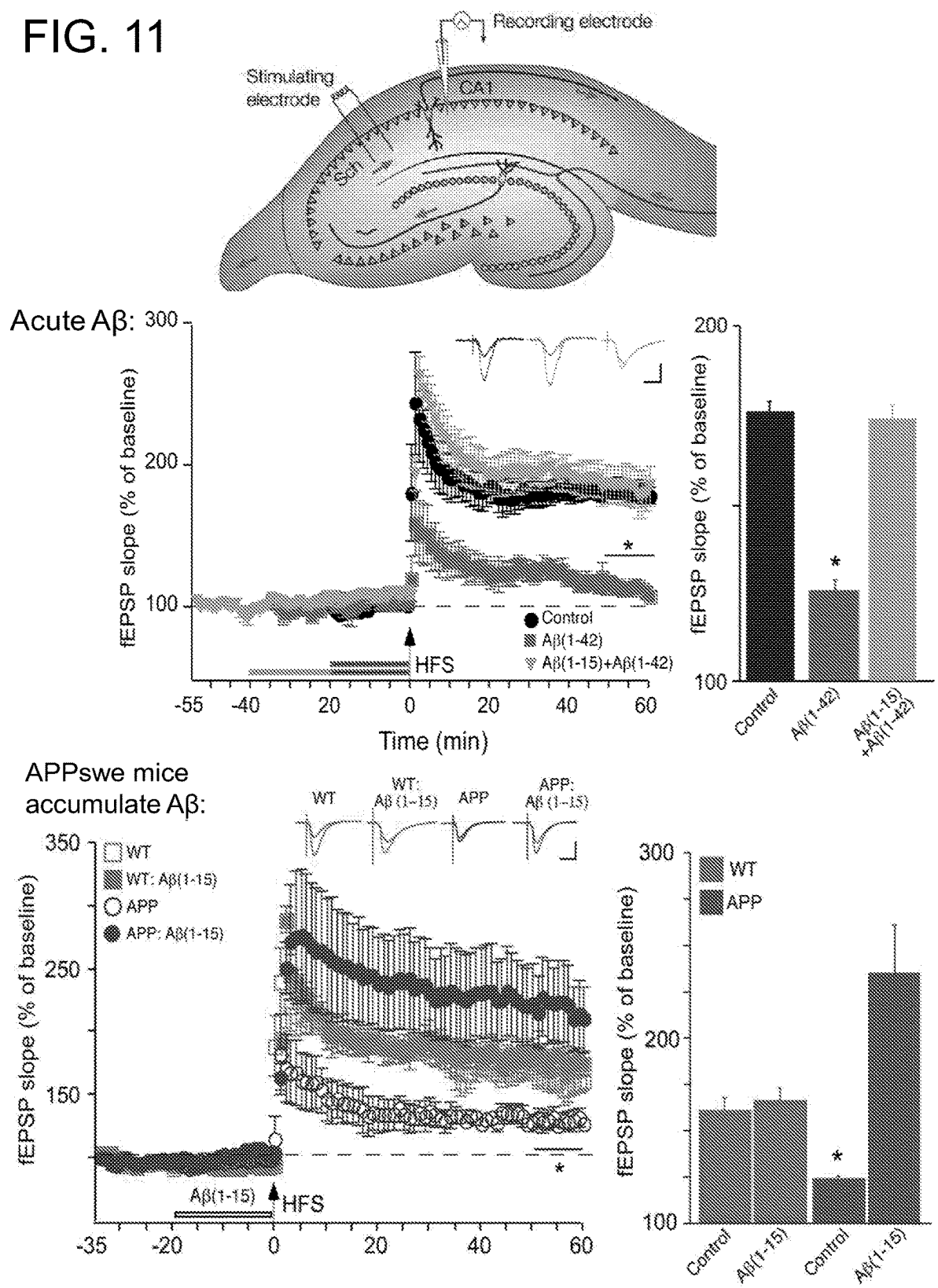
FIG. 11 shows that the N-Aβ fragment protects against Aβ-linked deficits in synaptic plasticity (from Lawrence et al., J Neurosci. 34, 14210-14218, 2014).
Figure 12:
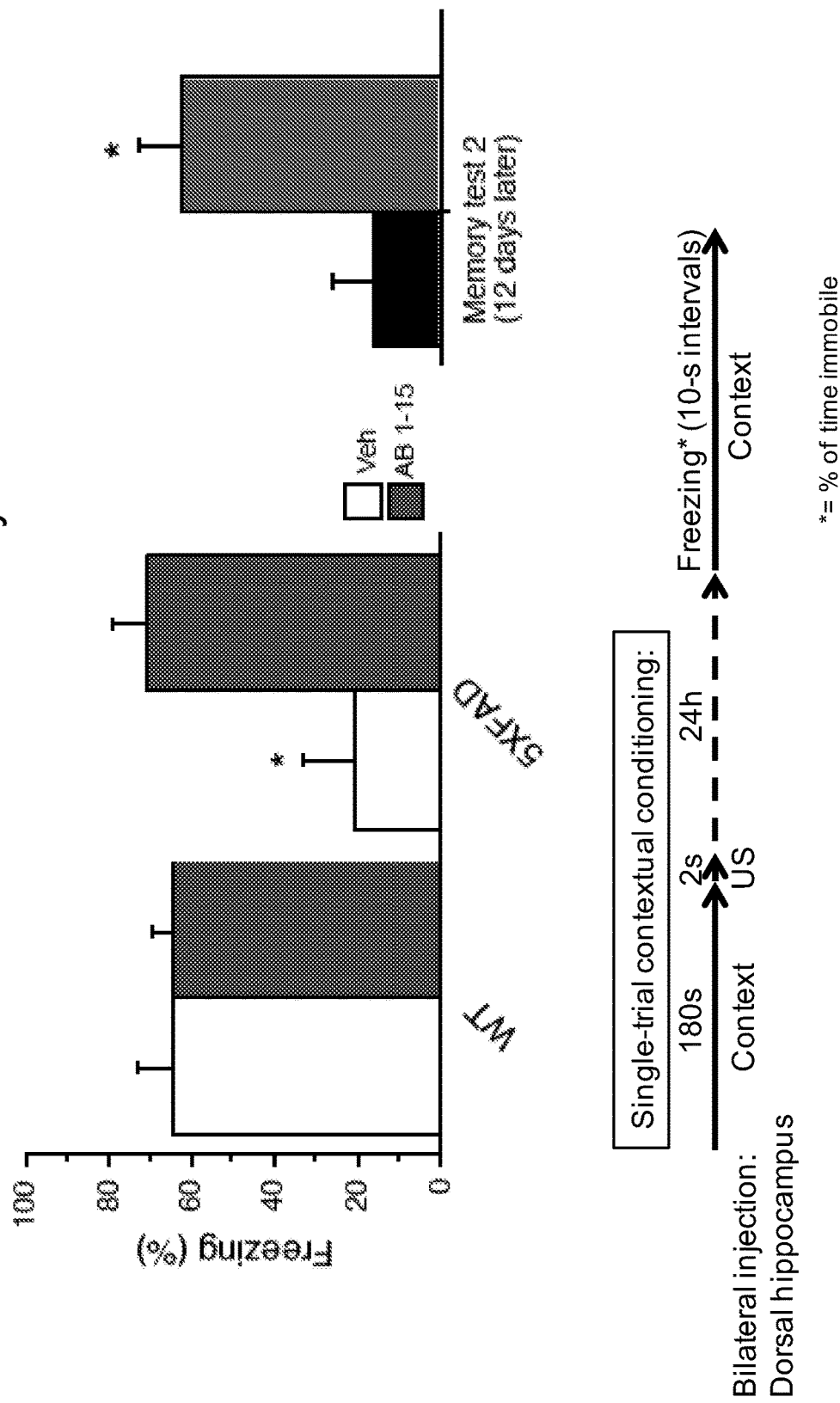
FIG. 12 shows that the N-Aβ fragment protects against Aβ-linked deficits in contextual fear memory in 5XFAD (familial Alzheimer's disease) APP mice.

Synaptic Function Assay. Extracellular recording of acutely isolated mouse hippocampal slices was performed to assess changes in synaptic plasticity as measured by changes in long-term potentiation. Slices under perfusion with artificial cerebrospinal fluid (aCSF) were stimulated via the Schaffer collateral axons (HFS: high-frequency stimulation), recording responses in the CA1 pyramidal cell region with or without prior perfusion with the N-terminal Aβ fragment. Non-limiting examples of results are shown in FIG. 11.

Cell Stress Assays. Cells were plated, differentiated and treated for 3 days poor to assay. Cell count and fluorescence intensity of reactive oxygen species (ROS)-positive cells were assessed as a means to measure cellular oxidative stress using an Image-IT® LIVE Green Reactive Oxygen Species Detection Kit. In brief, the cells were treated for three days for NG108-15 cultures end five or ten days for primary hippocampal neuronal cultures. The media was changed every day, thus replenishing with fresh Aβ every 24 h, unless otherwise noted. Thereafter, the cells were incubated with carboxy-H$_2$DCFDA (component A) at 37° C. for 30 min. During the last 5 min of incubation, 2 μg/ml of HOECHST stain (component B) was added to assess, in parallel, the integrity of the cell nuclei. The cells were washed twice with HBS and visualized using an Olympus IX81 epifluorescence microscope at excitation/emission of 495) 529 nm (ROS) and 350/461 nm (HOECHST), respectively. Exemplary results are shown in FIGS. 4, 5A, 6A, 7A-7B, 8, and 9A-9B.

Cell Survival. Cell survival was determined by counting cells everyday for 7 or 10 days of treatment. For each condition, all cells in 5 random fields of view were counted and averaged. Percent cell death was calculated based on daily cell counts as a proportion of starting cell count numbers (i.e. day 0).

Figure 14B:
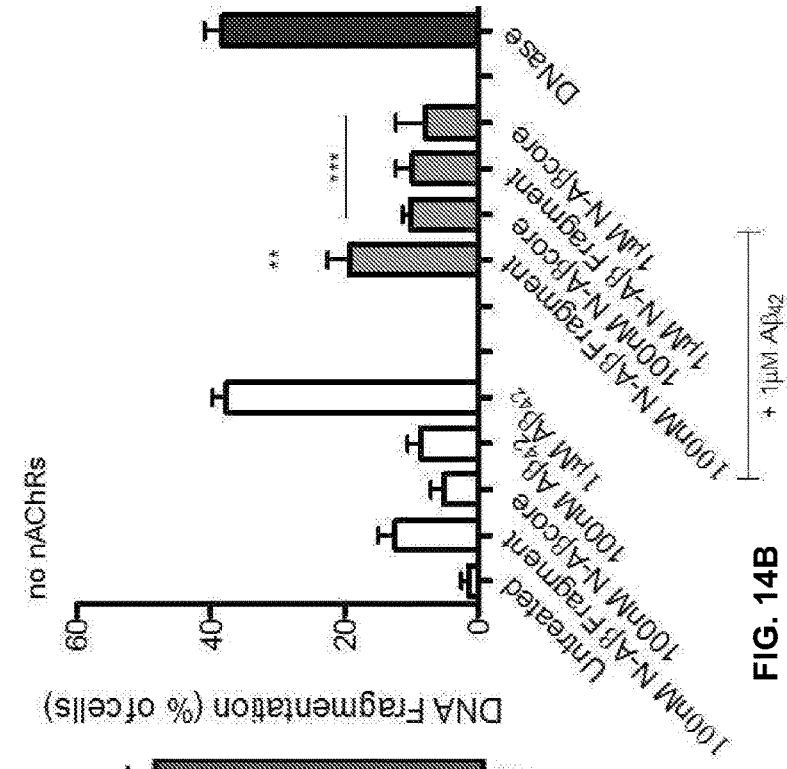
FIG. 14B shows daily treatment of 100 nM or 1 µM N-Aβcore or N-Aβ fragment alone and in combination with 1 µM Aβ1-42 (n=3 experiments). Note that in the absence of nAChRs, µM concentrations of Aβ1-42 are required to induce cell death. Co-treatments with Aβ are represented by closed (grey) bars.
Figure 14A:
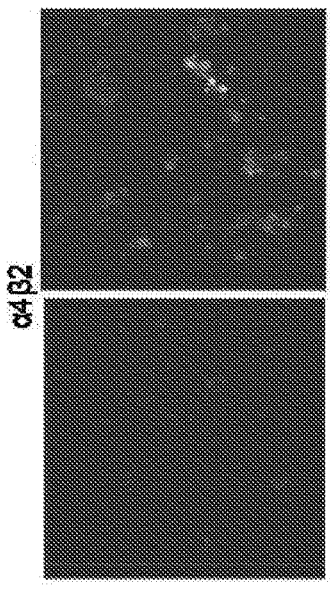
FIG. 14A shows co-treatment with 100 nM N-βcore after 0-, 1-, 2-, 3-day treatment of 100 nM Aβ1-42 in the presence of α4β2-nAGhRs (n=3 experiments), Mock-transfected cells are represented by open bars; α4β2-nAChR-transfected cells are represented by closed (grey) bars.
Figure 14A:
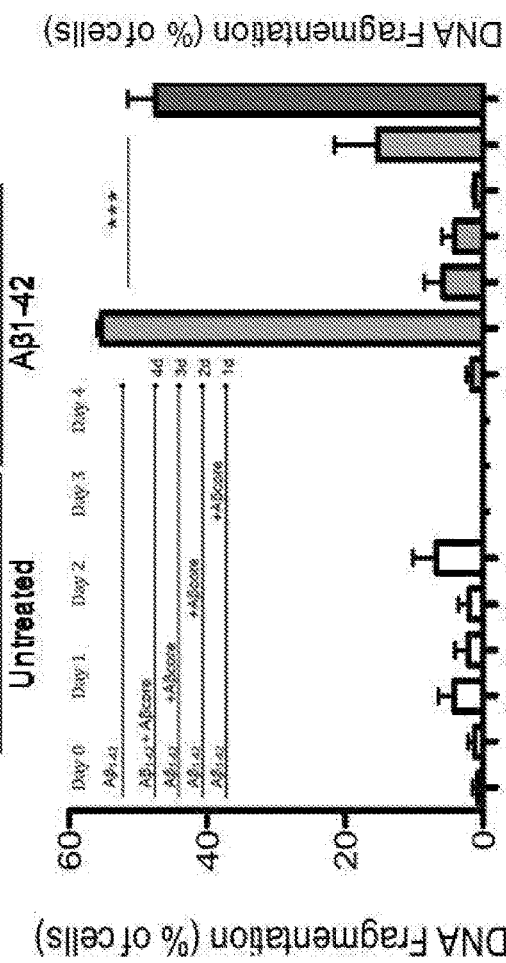

Cell Death (Apoptosis) Assay. Cells were plated, differentiated and treated for either 3 or 4 days prior to assay. Apoptotic cells were detected as DNA fragmentation by Click-IT TUNEL Alexa fluor 488. In brief, the cells were treated for four days, exchanging media each day. After the fourth day of treatment, the cells were fixed with freshly prepared 4% paraformaldehyde in PBS at room temperature for 20 min and permeabilized with Triton X-100 (0.25% in PBS) for another 20 min. The cultures were then washed twice and incubated with 50 μL of terminal deoxynucleotidyi transferase reaction buffer (Component A) for 10 min at room temperature. The buffer was replaced with TUNEL reaction mixture containing terminal deoxynucleotidyl transferase and incubated in a humidified chamber at 37° C. for 60 min. The cells were then washed three times with 3% BSA in PBS for 2 min each and then incubated with 50 μL of Click-iT reaction mixture (containing Alexa 488 azide) for 30 min at room temperature, protected from light exposure. The cells were again washed with 3% BSA in PBS and the cell nuclei were counterstained with Hoechst 33342 for 15 min at room temperature, protected from light. The coverstips were washed twice with PBS before mounting onto a slide with Vectashield mounting medium. Non-limiting examples of results are shown in FIG. 14A-14B.

Results

The N-A/βcore and the N-Aβ fragment protect against full-length Aβ-induced oxidative stress.

Figure 4:
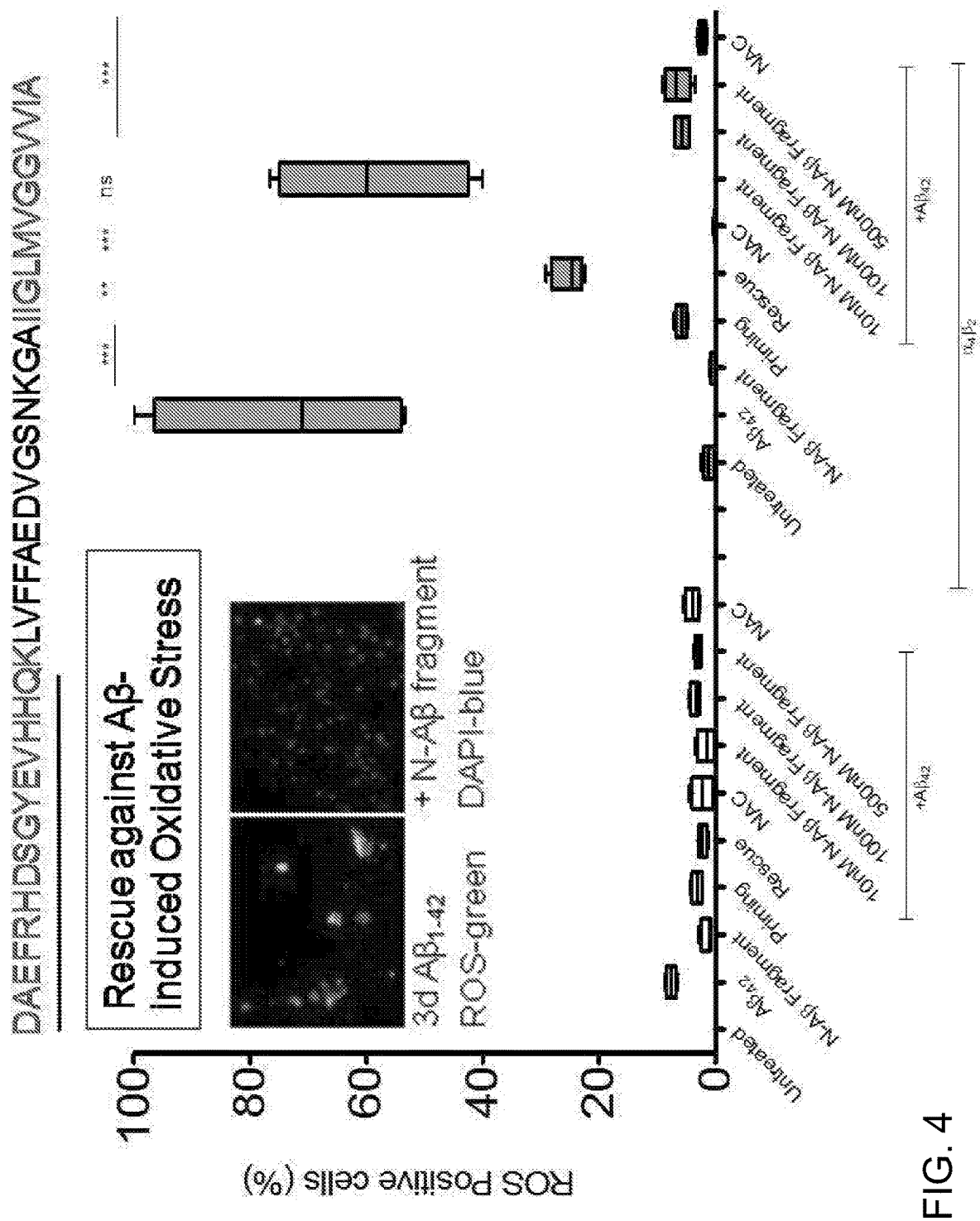
FIG. 4 shows that the N-Aβ fragment protects against Aβ-induced oxidative stress in the presence of high-affinity Aβ receptor (nicotinic receptors: nAChRs) in a differentiated neuronal cell line (NG108-15). Concentrations for combination daily treatments were 10 nM, 100 nM or 500 nM of either N-Aβ fragment or N-Aβcore in combination with 100 nM Aβ1-42. Timing experiments were performed with N-Aβ fragment (100 nM) introduced one day prior, co-treated, or 1 day post-treated with Aβ1-42 (100 nM) (n=4 experiments).
Figures 5A, 5B:
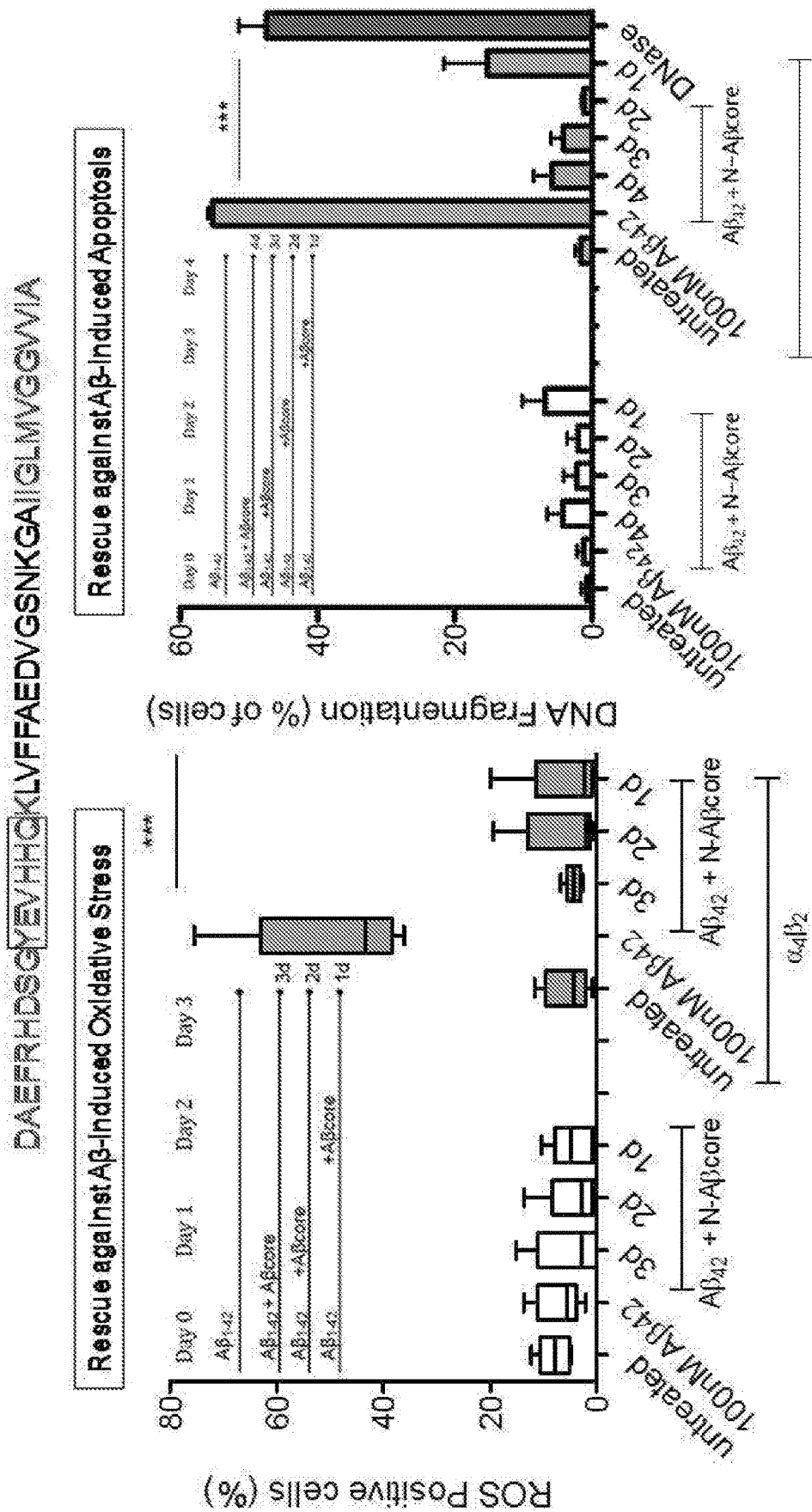
FIGS. 5A-5B show that the Aβ core sequence (N-Aβcore) protects against Aβ-induced cellular toxicity in the presence of high-affinity Aβ receptor.
Figures 6A, 6B:
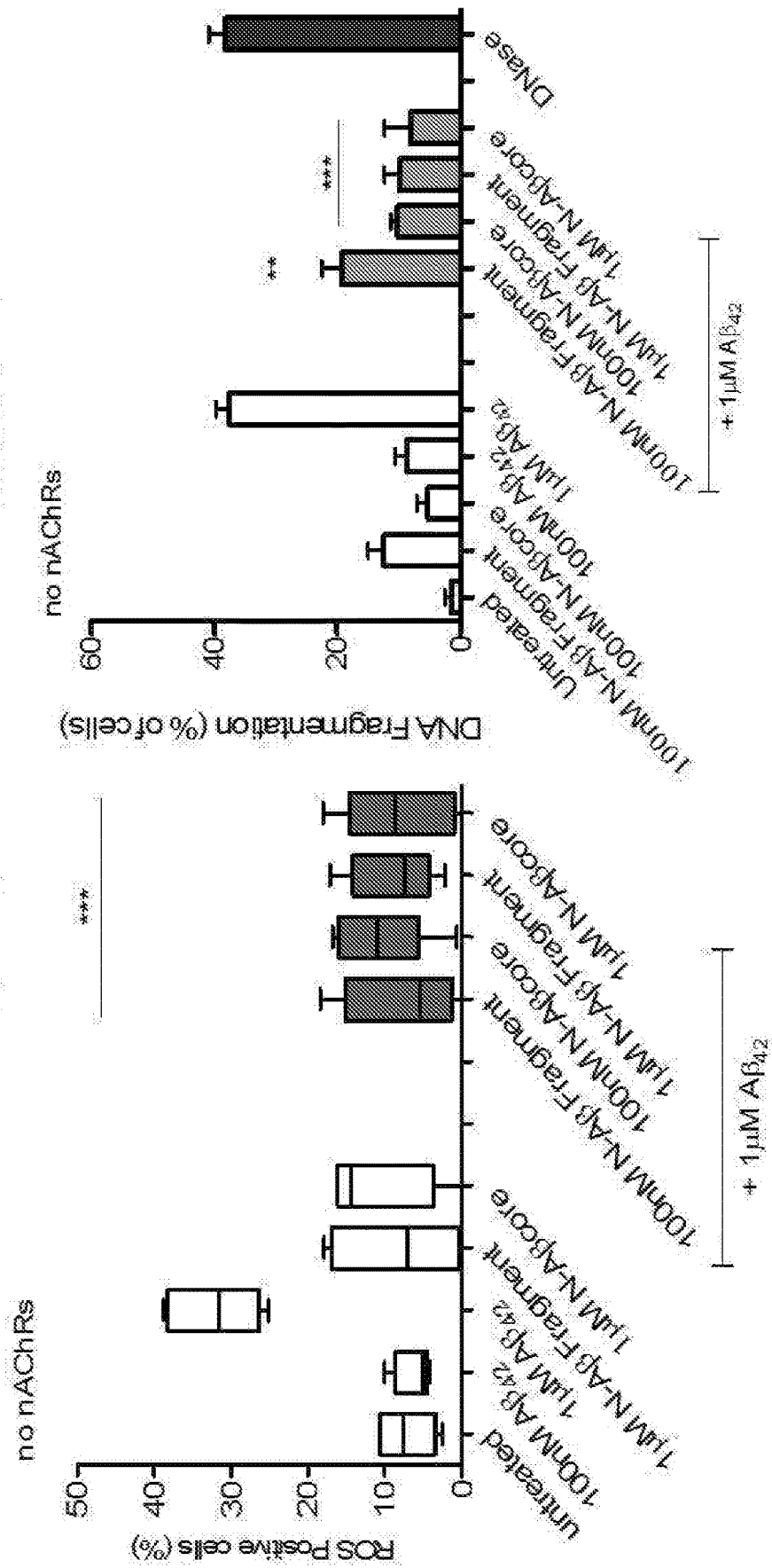
FIGS. 6A-6B show that the Aβcore sequence and N-Aβ fragment protect against Aβ-induced cellular toxicity in the absence of high-affinity Aβ receptor (nAChR).

To assess the potential neuroprotective effects of the non-toxic N-Aβcore, N-Aβcore mutants or N-Aβ fragment against Aβ1-42-induced toxicity, these indicators were assessed following administration of the N-terminal peptides under various conditions with daily treatment with 100 nM Aβ1-42. Co-treatment with the N-Aβ fragment at similar or higher concentrations was able to prevent Aβ1-42-induced oxidative stress (FIG. 4; p<0.0001). Priming (pre-treatment) with the N-Aβ fragment also significantly reduced Aβ1-42-induced ROS (FIG. 4; p<0.0001). The rescue treatment, in which the N-Aβ fragment was introduced into the culture 1 day after Aβ1-42, also attenuated ROS to a significant extent (FIG. 4; p<0.0001). In addition, treatment with a cell-permeant antioxidant, N-acetylcysteine (NAC) verified that the Aβ1-42-induced oxidative changes were the result primarily of reactive oxygen species. Turning to the N-Aβcore, co-treatment at nM concentrations or post-treatment (rescue) for 3-, 2-, or 1-day reduced Aβ1-42-induced ROS back to baseline levels (FIG. 5A; p<0.0001), suggesting that the N-Aβcore also protects against of Aβ1-42-induced toxicity, including late stages of oxidative stress.

In mock-transfected cells (absent nAChRs), higher concentrations (μM) of Aβ1-42 are required to induce significant levels of ROS. Co-treatment with nM-μM concentrations N-Aβcore or N-Aβ fragment reduced this oxidative stress compared to Aβ1-42 alone (FIG. 6A; p<0.0001), demonstrating that the N-Aβcore or N-Aβ fragment can protect against Aβ1-42-induced toxicity independently of α4β2-nAChRs. The inactive [H13A, H14A] and highly active [Q15H] Naβcore mutants were further examined on whether they had any protective effect on elevated oxidative stress from Aβ1-42. It was found that co-treatment with nM concentrations of the active mutant reduced ROS compared to Aβ1-42 alone (p<0.001), whereas the inactive mutant had no significant effect (FIG. 9A) at the concentration tested. These results substantiate the specificity of action of the N-βcore in neuroprotection against Aβ1-42-induced oxidative stress.

N-Aβcore and N-Aβ fragment protects against Aβ1-42-induced oxidative stress in primary hippocampal neurons.

Figures 7A, 7B:
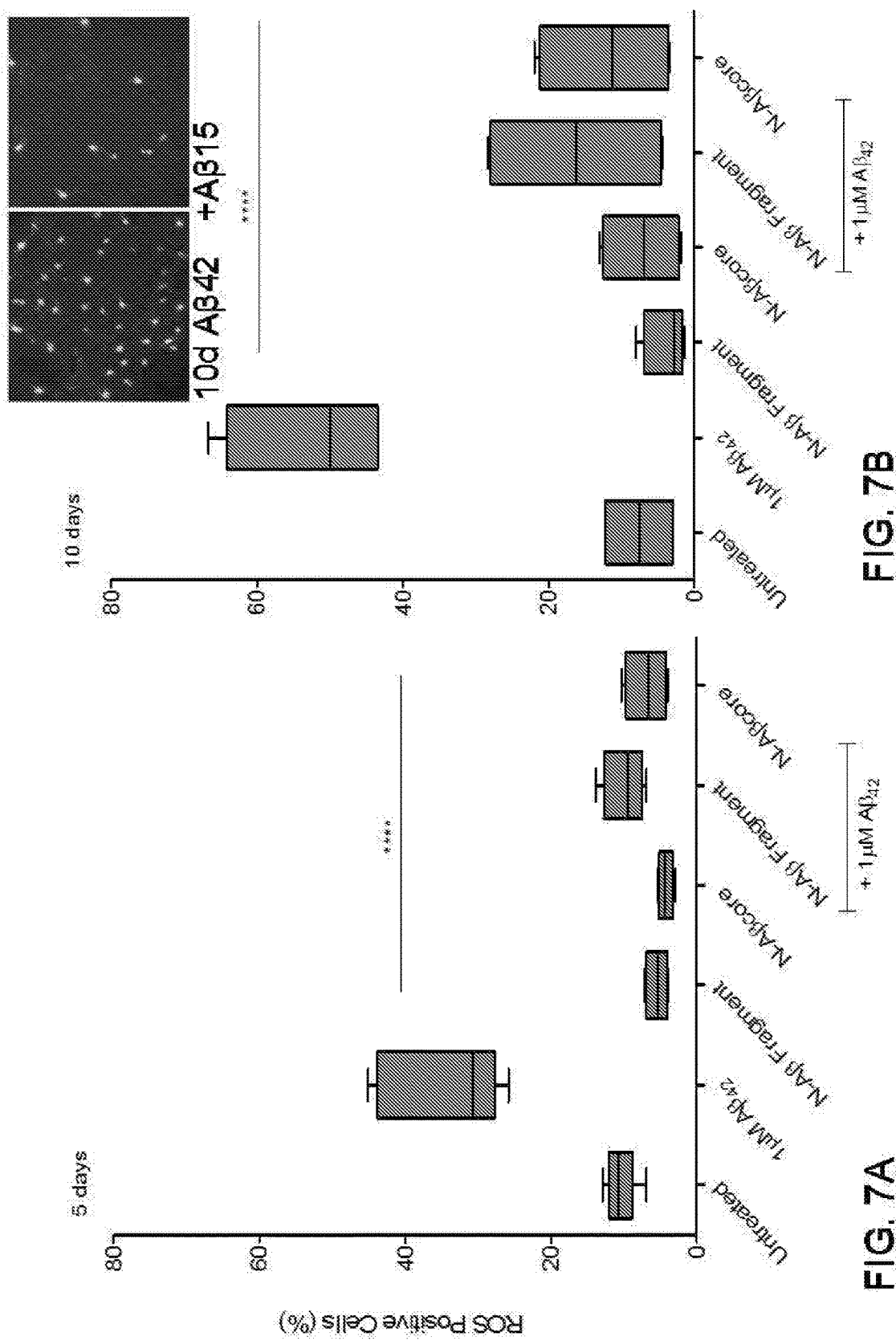
FIGS. 7A-7B show that the N-Aβ fragment and N-Aβ core sequence protect against Aβ-induced cellular toxicity (oxidative stress (ROS)) in mouse primary hippocampal neurons.

The experiments were repeated in primary hippocampal cultures to assess the protective action of N-Aβ fragment or N-Aβcore in a relevant primary neuronal model. Primary mouse hippocampal neuron cultures were either treated daily with 1 μM Aβ1-42, N-Aβ fragment or N-Aβ core alone, or co-treated with Aβ1-42 and N-Aβ fragment or N-Aβcore for 5 days (FIG. 7A) or 10 days (FIG. 7B). As expected, treatment with 1 μM Aβ1-42 resulted in 40-50% ROS-positive cells at five days and close to 70% ROS-positive cells at 10 days across the cell population. Co-treatment of cultures with 1 μM Aμ1-42 and 1 μM N-Aβ fragment or 1 μM N-Aβcore reduced the levels of ROS down to untreated (baseline) levels when compared to daily treatment with Aβ1-42 alone (p<0.0001), demonstrating that the N-terminal Aβ peptides were also able to fully protect against Aβ-induced oxidative stress in primary neurons.

Prolonged exposure to N-βcore or NA-β fragment protects against Aβ1-42-induced apoptosis.

In addition to inducing oxidative stress, expression of α4β2-nAChRs sensitizes differentiated neuroblastoma NG108-15 cells to Aβ1-42-induced apoptosis, while elevated Aβ1-42 triggers apoptosis in the absence of nAChRs. Therefore, N-Aβcore or N-Aβ fragment were further assessed on whether they can protect against Aβ1-42-induced apoptosis with or without the presence of α4β2-nAChRs. Co-treatment with nM concentrations of the N-Aβcore in the presence α4β2-nAChRs on day 1, 2 or 3 following the start of daily Aβ1-42 treatment reduced apoptosis compared to Aβ1-42 alone (p<0.0001), as measured by TUNEL staining for apoptotic cells (FIG. 14A), suggesting that the N-Aβcore can protect against late stages of Aβ1-42-induced neuronal death. In addition, high concentrations of Aβ1-42 induced apoptosis in the absence of the sensitizing α4β2-nAChRs, and co-treatments with nM-μM concentrations. N-Aβcore or N-Aβ fragment over four days also reduced DNA-fragmentation compared to Aβ1-42 alone (p<0.0001 for 100 nM and 1 μM N-Aβcore; p<0.001 and p<0.0001, 100 nM and 1 μN-Aβ fragment, respectively), with a trend of greater reduction at μM concentrations (FIG. 14B). This indicates that the N-Aβcore or N-Aβ fragment can also protect against Aβ1-42-induced neuronal death independently of the α4β2-nAChRs.

N-Aβcore and N-Aβ fragment protect against Aβ1-42-induced cell death.

Figure 10A:
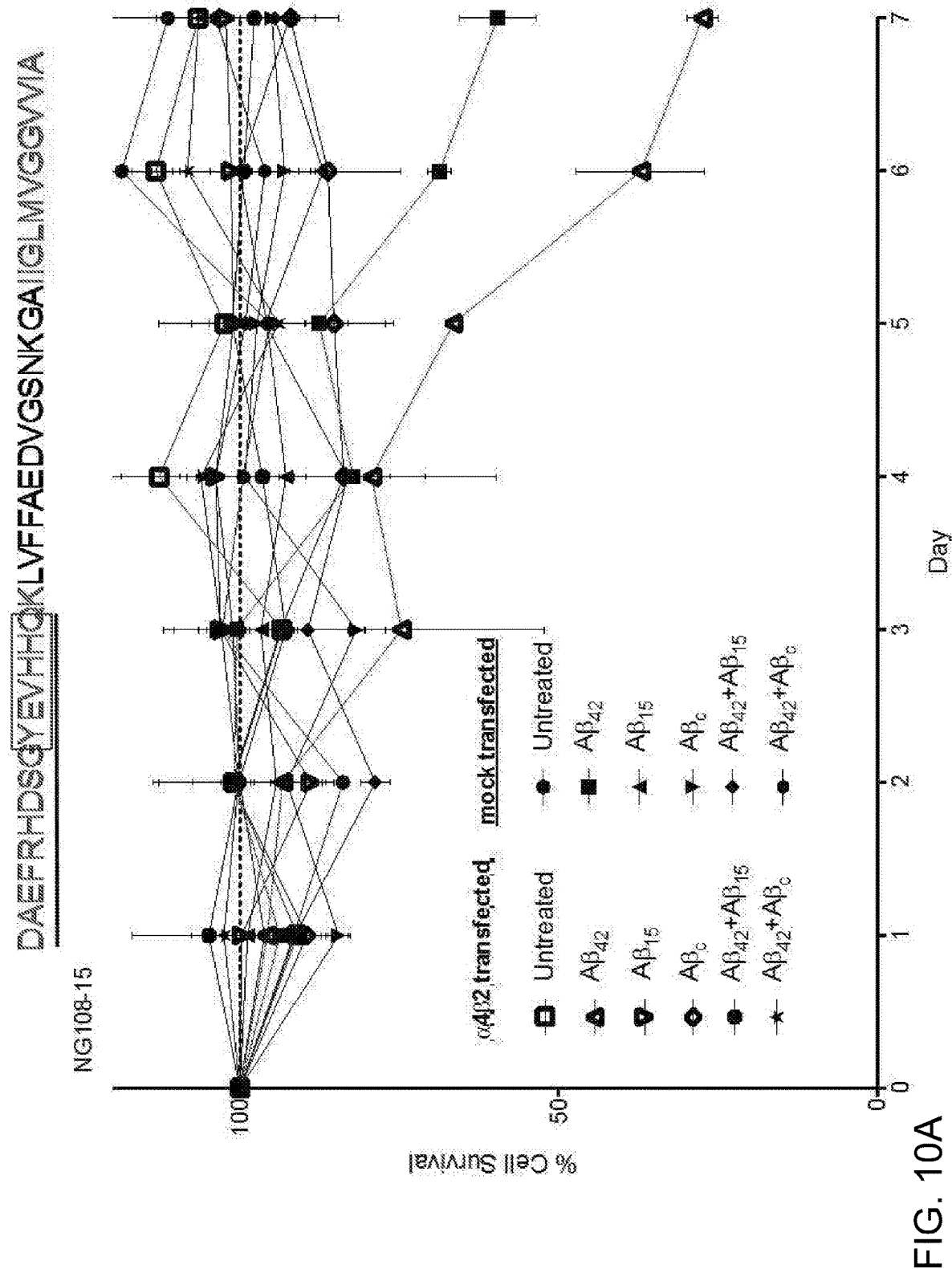
FIGS. 10A-10B show that the N-terminal Aβ fragment is non-toxic and protects against Aβ-induced cell death.
Figure 10B:
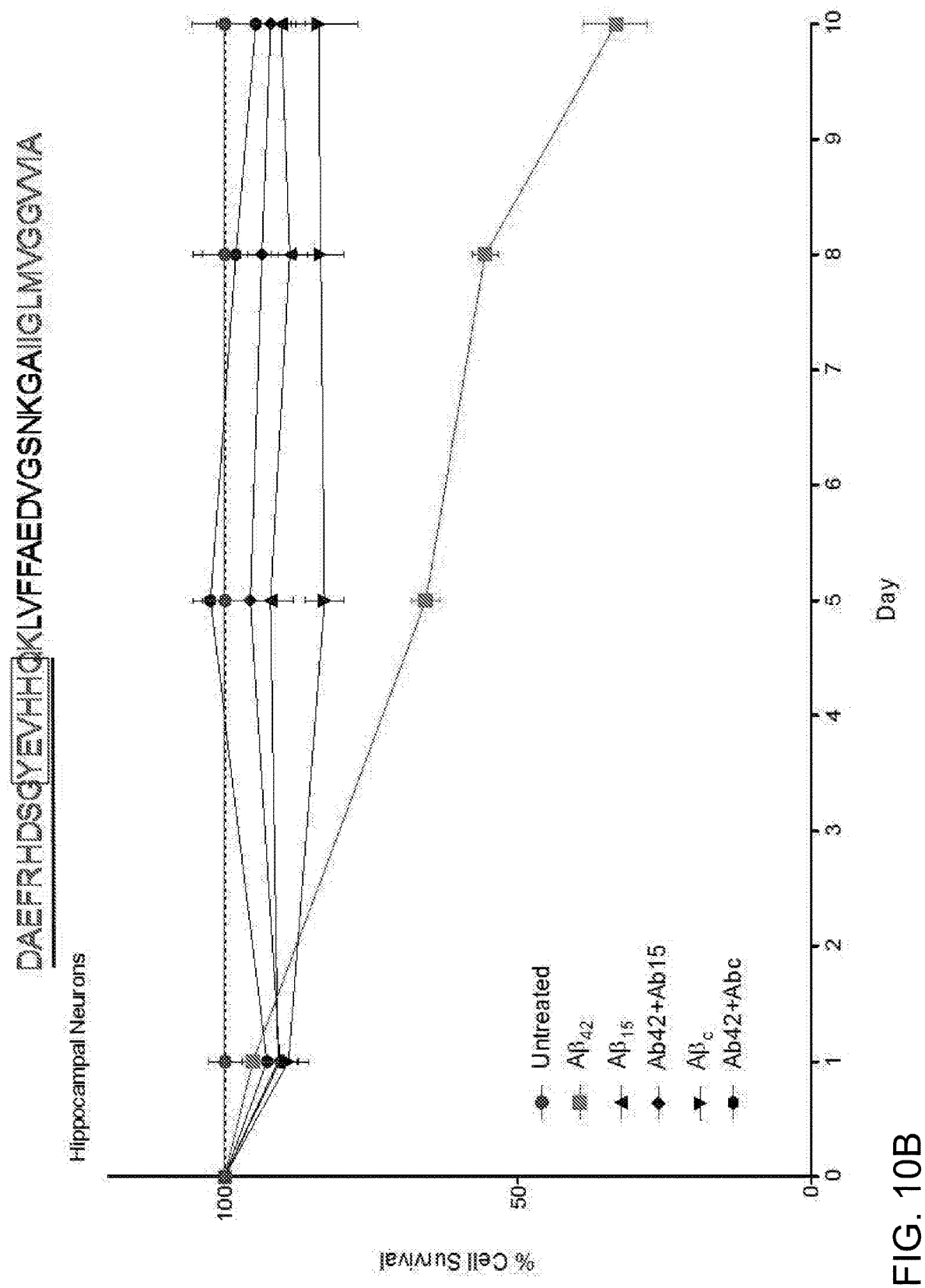

In cell survival assays, the impact of co-treatments with N-Aβ fragment or N-Aβcore on Aβ1-42-induced cell death was assessed for cultures of either differentiated NG108-15 cells or mouse hippocampal neurons over 7- or 10-days through cell counts. As expected, 7-day cell counts in NG108-15 cultures showed significant cell death in α4β2-nAChR-transfected cells treated with Aβ1-42 alone (FIG. 10A). Co-treatment with 100 nM N-Aβcore as well as the N-Aβ fragment was able to fully protect against Aβ1-42-induced cell death at 7 days compared to Aβ1-42 alone (p<0.0001). Similarly, at high concentrations (1 μM), both N-Aβ fragment and N-Aβcore protected primary hippocampal neurons against β1-42-induced cell death over 10-day treatments compared to Aβ1-42 alone (FIG. 10B p<0.0001).

Stabilization of N-Aβcore retains its receptor-linked $Ca^{2+}$ activity end protects against Aβ1-42-induced neurotoxicily in α4β2-nAChR-transfected cells.

To protect the N-Aβcore from exopeptidase degradation in vivo, the N-terminus was capped with an acetyl group and its C-terminus with an amide group. Relative to the N-Aβcore, the capped-N-Aβcore retained its potent activity (FIG. 13B), with a trend towards an increased $Ca^{2+}$ response. To further protect the N-Aβcore from endopeptidase activity, the enantiomeric conversion from the L-configuration to the D-configuration for each amino acid retained activity (FIG. 13B). In addition, the stabilized N-Aβcore, at nM concentrations, was as neuroprotective against Aβ1-42-induced oxidative stress as the N-Aβcore (FIG. 9B; p<0.05 vs. Aβ1-42 alone), indicating the potential for use of the stabilized peptide in vivo.

The present inventions demonstrates that treatment with the N-Aβ fragment or N-Aβcore can effectively and potently protect against Aβ1-42-induced oxidative stress and apoptosis. Remarkably, treatment with the N-Aβ fragment or N-Aβcore after the induction of oxidative stress by Aβ1-42 also rescued the cells from this neurotoxicity. Furthermore, the fragment or N-Aβcore were also protective against neurotoxicity induced by high concentrations of Aβ1-42 in the absence of sensitizing nAChRs, again either with co-treatment or post-treatment rescue. In addition, only high levels (μM) of the N-Aβ fragment protected against excitotoxicity in present model neuronal cultures. Together, these findings would suggest that the N-Aβ fragment and N-Aβcore may be neuroprotective through altered binding of Aβ1-42 for key target sites and/or activation of alternative pathways, such as an anti-apoptotic pathway and/or anti-oxidative pathway, blocking or reversing the process by which Aβ1-42 induces neurotoxicity.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A modified, neuroprotective β-amyloid peptide analogue for use in treating Alzheimer's Disease, wherein the peptide analogue comprises a sequence at least 50% identical to YEVHHQ (SEQ ID NO. 1), with the caveat that Y is preserved and HH is preserved, wherein a backbone amide of at least one of the residues in the peptide analogue is N-methylated, wherein the peptide analogue ends at the Q of SEQ ID NO. 1.

2. The peptide analogue of claim 1, wherein at least one of the residues in SEQ ID NO. 1 is a D-amino acid, a β-substituted amino acid, or a peptide isostere.

3. The peptide analogue of claim 1, wherein the sequence is at least 60% identical to SEQ ID NO. 1.

4. The peptide analogue of claim 1, wherein the sequence is at least 80% identical to SEQ ID NO. 1.

5. The peptide analogue of claim 1, wherein the peptide analogue is non-toxic and provides protective activity against β-amyloid toxicity.

6. The peptide analogue of claim 1, wherein the peptide analogue comprises an N-terminal modification, a C-terminal modification, or both.

7. The peptide analogue of claim 1, wherein the peptide analogue is cyclized.

8. The peptide analogue of claim 1, wherein the Q residue is conservatively substituted with H.

9. A modified, neuroprotective β-amyloid peptide analogue of DAEFRHDSGYEVHHQ (SEQ ID NO. 2) for use in treating Alzheimer's Disease, wherein the peptide analogue comprises a sequence according to the following:

$$X_1X_2X_3X_4X_5X_6X_7X_8X_9YX_{11}X_{12}HHX_{15}$$ (SEQ ID NO. 3)

wherein Y and HH are preserved, wherein the $X_1$-$X_9$ residues are optionally present in the peptide analogue, wherein the $X_1$-$X_9$, $X_{11}$-$X_{12}$, and $XD_{15}$ residues are each independently selected from natural and unnatural amino acids, wherein a backbone amide of at least one of the residues in the peptide analogue is N-methylated, wherein the peptide analogue ends at the $X_{15}$ residue.

10. The peptide analogue of claim 9, wherein the peptide analogue is at least 60% identical to YEVHHQ of SEQ ID NO. 2.

11. The peptide analogue of claim 9, wherein the peptide analogue is at least 80% identical to YEVHHQ of SEQ ID NO. 2.

12. The peptide analogue of claim 9, wherein at least one of the residues in SEQ ID NO. 3 is a D-amino acid, a β-substituted amino acid, or a peptide isostere.

13. The peptide analogue of claim 9, wherein the peptide analogue is non-toxic and provides protective activity against β-amyloid toxicity.

14. The peptide analogue of claim 9, wherein the peptide analogue comprises an N-terminal modification, a C-terminal modification, cyclization, or a combination thereof.

15. The peptide analogue of claim 9, wherein $X_{15}$ is H.

16. A modified, neuroprotective β-amyloid peptide analogue comprising a sequence at least 60% identical to YEVHHX (SEQ ID NO: 7), wherein X is H, with the caveat that HHH is preserved, wherein a backbone amide of at least one of the residues in the peptide analogue is N-methylated.

* * * * *